(12) United States Patent
Dellaporta et al.

(10) Patent No.: US 9,258,998 B2
(45) Date of Patent: Feb. 16, 2016

(54) METHODS FOR CONTROLLING FLOWER DEVELOPMENT IN PLANTS

(75) Inventors: Stephen L. Dellaporta, Branford, CT (US); Ivan F. Acosta, Bogota (CO)

(73) Assignee: Yale University, New Haven, CT (US)

( * ) Notice: Subject to any disclaimer, the term of this patent is extended or adjusted under 35 U.S.C. 154(b) by 209 days.

(21) Appl. No.: 13/142,819

(22) PCT Filed: Jan. 8, 2010

(86) PCT No.: PCT/US2010/020505
§ 371 (c)(1),
(2), (4) Date: Sep. 26, 2011

(87) PCT Pub. No.: WO2010/081005
PCT Pub. Date: Jul. 15, 2010

(65) Prior Publication Data
US 2012/0010077 A1   Jan. 12, 2012

Related U.S. Application Data

(60) Provisional application No. 61/143,394, filed on Jan. 8, 2009.

(51) Int. Cl.
*A01H 5/00* (2006.01)
*A01H 3/04* (2006.01)
*A01H 1/00* (2006.01)
*A01N 37/42* (2006.01)

(52) U.S. Cl.
CPC ..................................... *A01N 37/42* (2013.01)

(58) Field of Classification Search
USPC ........................................................ 800/283
See application file for complete search history.

(56) References Cited

U.S. PATENT DOCUMENTS 3,855,219 A      12/1974  Fuchs et al.
6,114,284 A  *   9/2000   Fujisawa et al. .............. 504/140

FOREIGN PATENT DOCUMENTS

WO           97/10703         3/1997
WO       WO 9710703 A1 *     3/1997

OTHER PUBLICATIONS

Acosta et al, tasselseed1, is a lypoxygenase affecting jasmonic acid signaling signaling in sex determination of maize, Science (2009) 323:262-265.*
Dellaporta et al, Sex determination in flowering plants, Plant Cell (1993) 5:1241-1251.*
Hultquist et al, Feminized tassels of maize mop1 and ts1 mutants exhibit altered levels of miR156 and specific SBP-box genes, Planta (2008) 229:99-113.*
Calderon-Urrea, et al., "Cell death and cell protection genes determine the fate of pistils in maize," *Development*, 1999, 126:435-441.
Acosta, et al., "*tasselseed1* Is a Lipoxygenase Affecting Jasmonic Acid Signaling in Sex Determination of Maize," *Science*, 2009, 323:262-265.
Sanders, et al., "The Arabidopsis *Delayed Dehiscence1* Gene Encodes an Enzyme in the Jasmonic Acid Synthesis Pathway," *The Plant Cell*, 2000, 12:1041-1061.
Cheng, et al., "Effects of 3-(*p*-chlorophenyl)-6-methoxy-*s*-triazine-2,4 (1H, 3H) dione triethanolamine (DPX-3778) treatment on the floral development of maize," *Can. J. Bot.*, 1989, 67(2): 327-331.
Johnson, et al., "Chemical Control of Pollination in Wheat and Oats," *Crop Science*, 1975, 16(4):584-587 (Abstract only).
Hanna, "Effect of DPX 3778 on Anther Dehiscence in Pearl Millet," *Crop Science*, 1977, 17(6):965-967 (Abstract only).
Johnson, et al., "Use of DPX 3778 to Produce Hybrid Wheat Seed," *Crop Science*, 1978, 18(6):1026-1028 (Abstract only).
International Search Report for PCT/US10/20505, dated May 3, 2010.
International Preliminary Report on Patentability for PCT/US10/20505, dated Jul. 12, 2011.
Goff, S.A. et al., "A Draft Sequence of the Rice Genome (*Oyrza sativa* L. ssp. *japonica*)," Science, 2002, pp. 92-100, vol. 296.
Strable, J. et al., "Maize (*Zea mays*): A Model Organism for Basic and Applied Research in Plant Biology," Cold Spring Harb Protoc, 2009, pp. 1-9, vol. 4, No. 10.

* cited by examiner

*Primary Examiner* — Shubo (Joe) Zhou
*Assistant Examiner* — Mykola Kovalenko
(74) *Attorney, Agent, or Firm* — Saul Ewing LLP; Kathryn Doyle; Domingos J. Silva

(57) ABSTRACT

The present invention provides a method of controlling the sexuality of a plant comprising treating the plant with a composition comprising a compound selected from the group consisting of jasmonic acid, a jasmonic acid derivative, and a salt thereof.

5 Claims, 15 Drawing Sheets

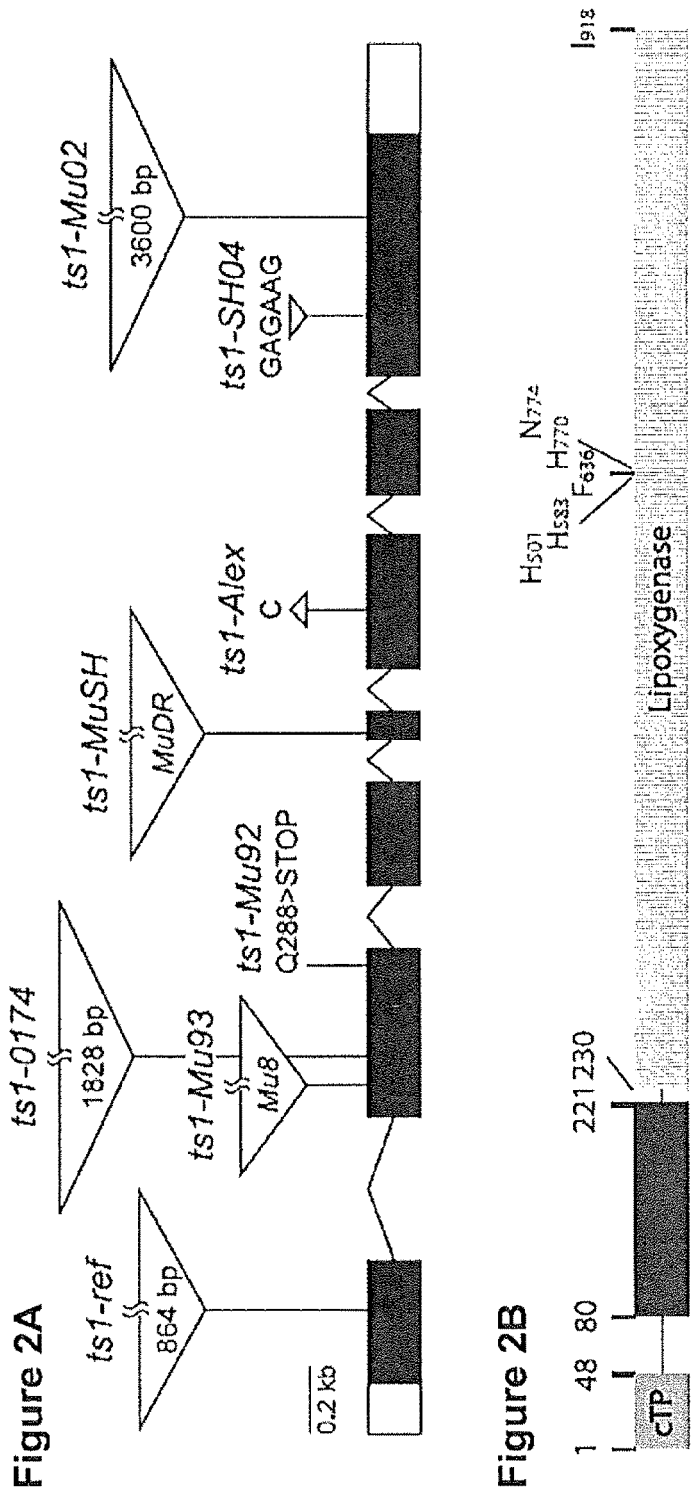

Figure 4A

TS1:    SEQ ID NO:20
TS1b:   SEQ ID NO:21
StLOX5: SEQ ID NO:22
GmLOX1: SEQ ID NO:23

Figure 4B

```
TS1     RRMRIGRPKIIDDRAESRVEYPEPIYVSRDEEFELGKNEMLSEGALKALIENEMPLLVSSVSPDIR--DEAGEHIVDNLEKEGLRLKQALQDQLEQKIP   390
TS1b    RRMRIGREKIIDDRAESRVEYPEPIYVSRDEEFEGGKNEMLSEGALKALIENEMPLLVSSVSPDIR--DEAGEHIVDNLEKEGLRLKQALQDQLEQKIP   389
StLOX5  RRCRSGRTPLDID-SAESRVEKRNP-YVPRDEQEEFSKMITFSSRLEAVLENLIPSMASISSNNE--DEKGFSDIDNLYSKGLLKLGLQDEVZKKIP    386
GmLOX1  RRGRIGRGPFVDNNEKQGET----IVEPRDENGHLKSKDALE-G-KSLSCIWQRFESAFDLKSFIRESEQWEDLKEGGIKFRDVISHIF-LP        381

TS1     EVTKIQENSEG-ILRVDTPDIIKQEFAFLRDEEFAQALAGINPDVNIERLQAFPMSKLDPAVYGPPESAIIEEHIGQLDGMSVQQALCDRIYMLDY    489
TS1b    EVTKIQENSEG-ILRVDTPDIIKQEFAFLRDEEFAQALAGINPDVNIERLQAFPMSKLDPAVYGPPESAIIEEHIGRLDGMSVQQALEDNRLYMLDY    487
StLOX5  LPKTVSSIEGCILKDTPKILSKDKEAFLSKDKEAFLQFTPPFVSKLDPEIYGPPESALIEEHIQFHHNGMIVQEALCANKIEVTDH              486
GmLOX1  IKELVRDSGGHLKFQPEVVQFSQSARMIDEEFARENLAGVNPCVIRGLEEEPRKSNDPAIYGLQSSITADSI---DLRGVIMDEALGSRRLFMLDY    405

TS1     EDIFMPELDRINALDGRKAVGTRDLFLTLTLGTIKPIAIELCLPEMTEGCARAK-RVFTPPADAISNWLKQLAKAEVCSNDAGVEQLINEMLRIEHAMEP   583
TS1b    EDIFPFLDRINAQDGRKAVGTRDLFELIGAGTLKPIAIELRLPPMTEGCARAK-RVLTPPADAISNWTKQLAKAEVCSNDAGVEQLINERLRIEH.JEP   586
StLOX5  EDVITPELDRINKAVATRTFFISDVGTLKPIAIELSLP-CTGPS SRSK-RVTFPPVCRI-NWEWQIAKSHUCANDAGVHQLVNEMLDTHLSIEP        584
GmLOX1  EDIFMPTVRQINQLNSAKTYATRRILKELRELEGKKFVAIELSIPHSAGDISAWSQUVDAKEGVESBIWLEAKNTV-VNDSCYEQLMSHHNTRRAMEP    505
```

TS1:    SEQ ID NO:20
TS1b:   SEQ ID NO:21
StLOX5: SEQ ID NO:22
GmLOX1: SEQ ID NO:23

Figure 4C

TS1:    SEQ ID NO:20
TS1b:   SEQ ID NO:21
StLOX5: SEQ ID NO:22
GmLOX1: SEQ ID NO:23

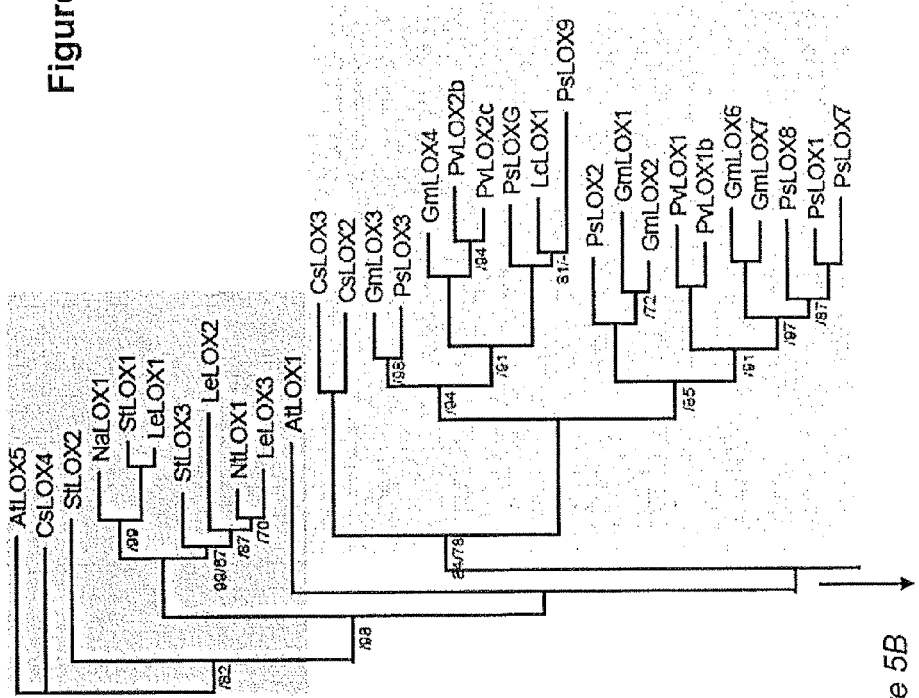

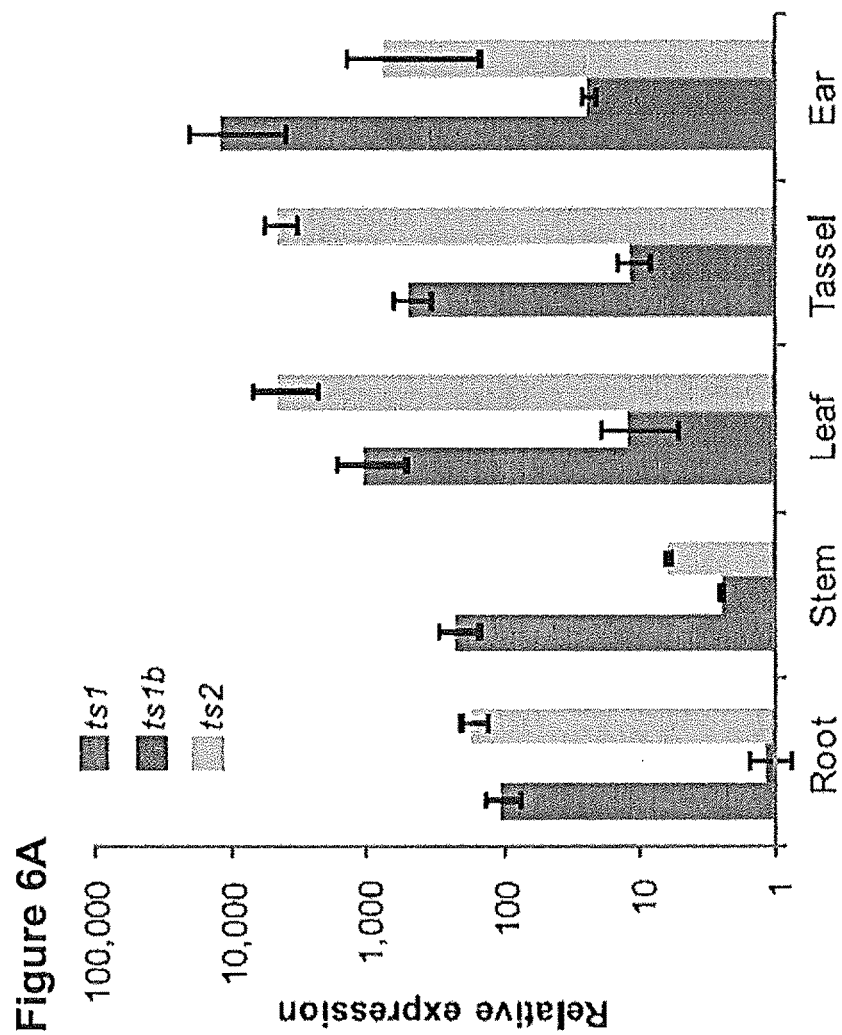

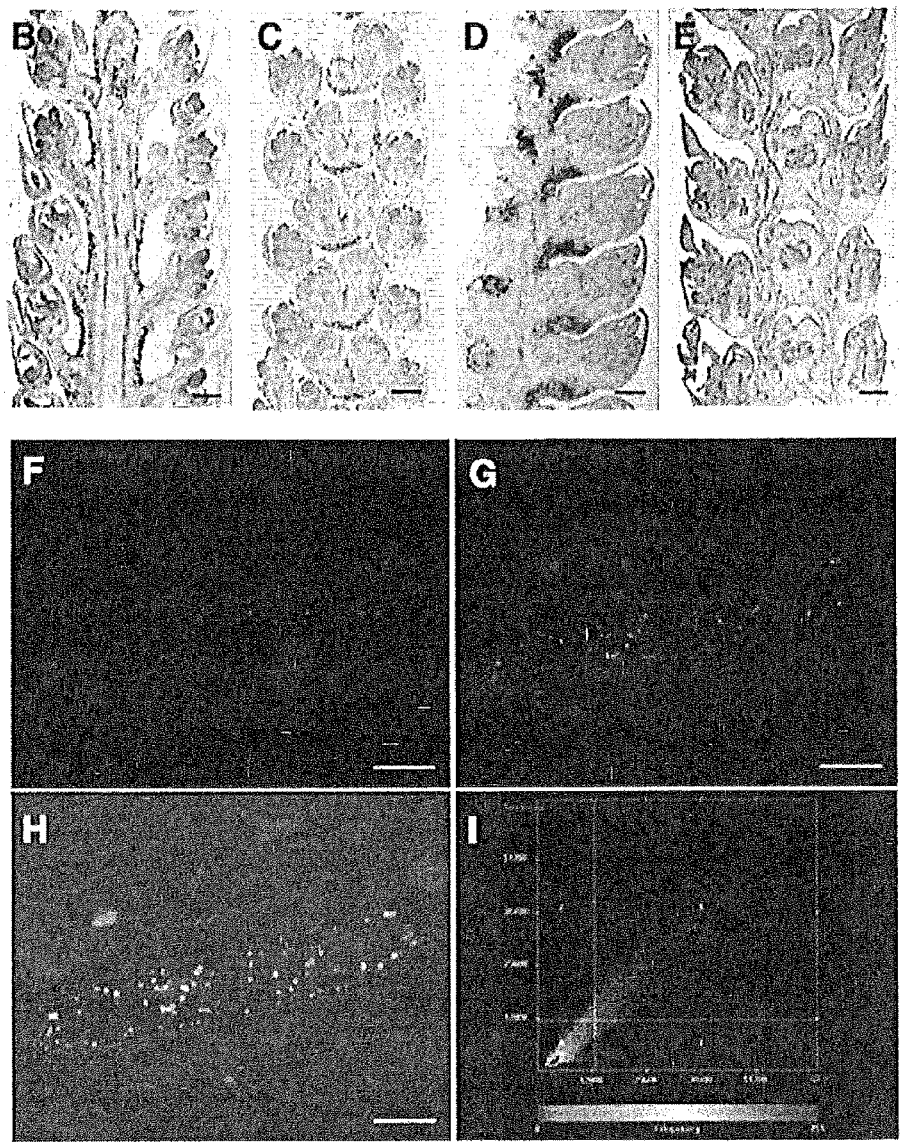
Figures 6B-I

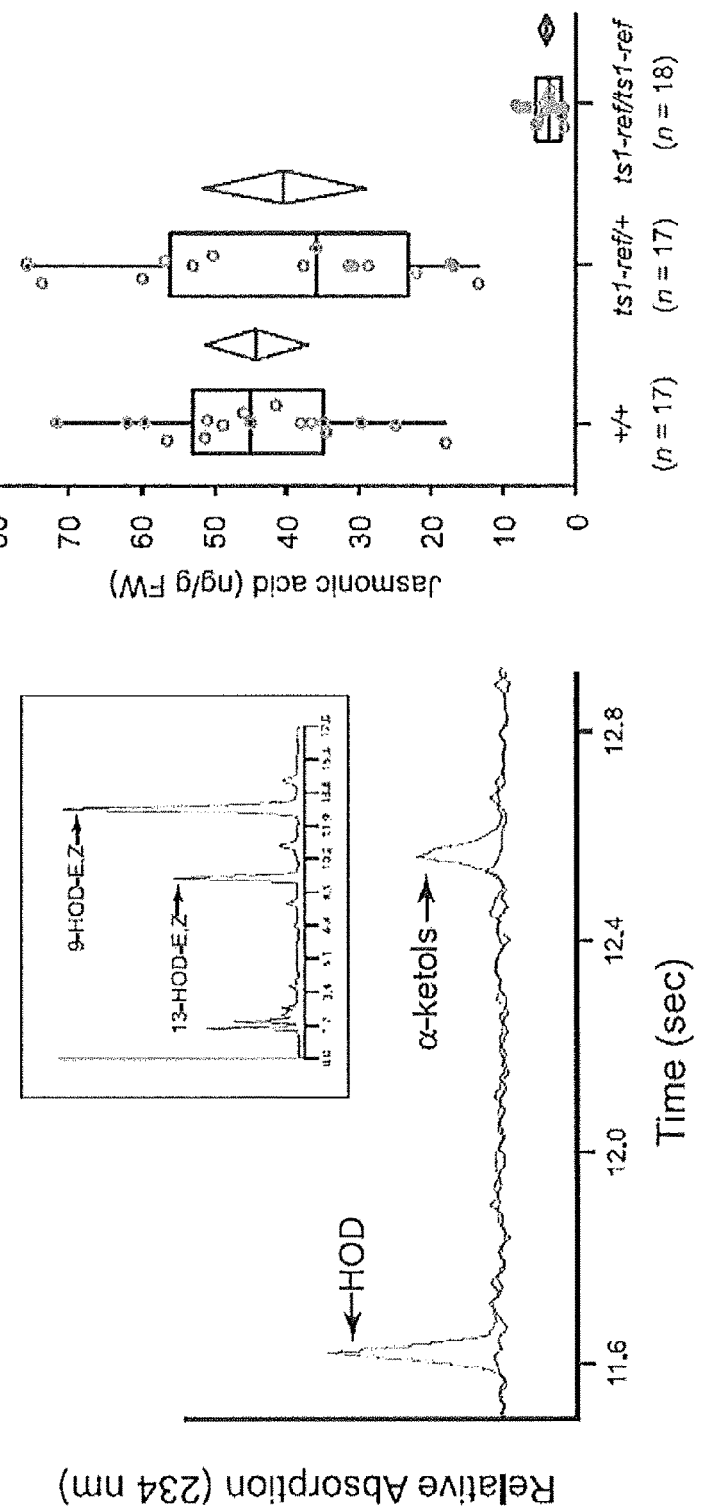

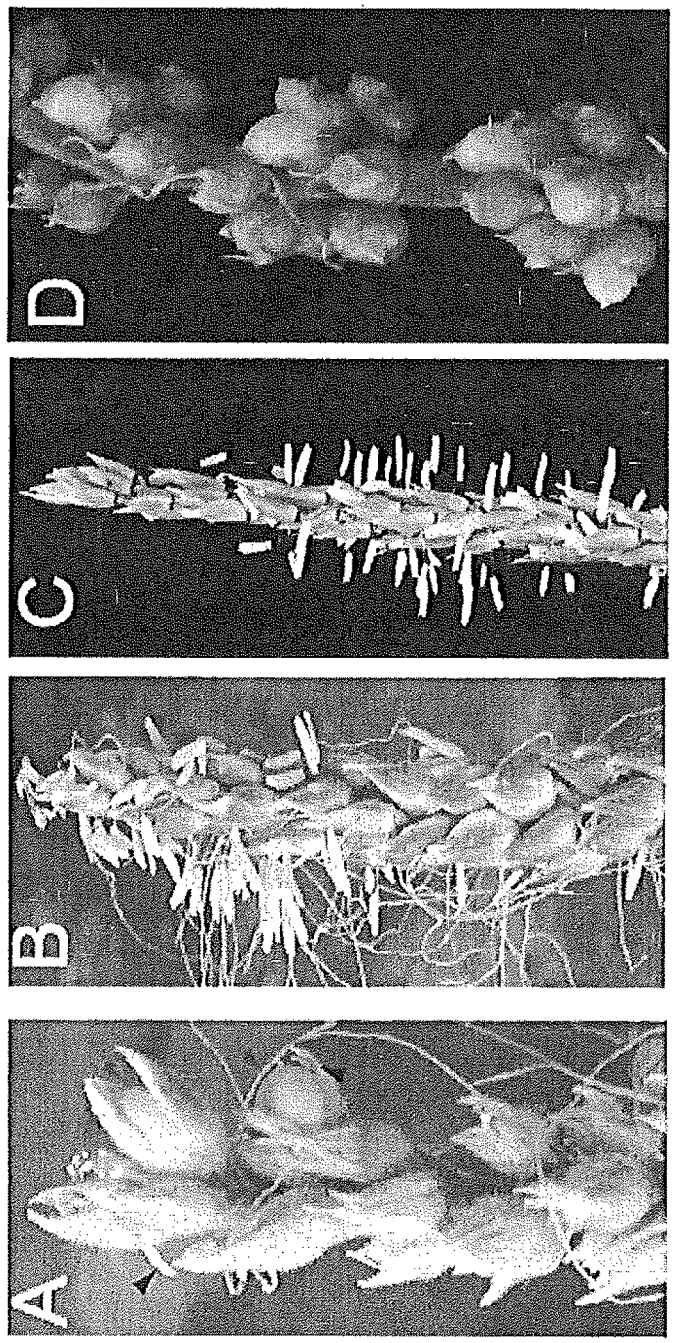

METHODS FOR CONTROLLING FLOWER DEVELOPMENT IN PLANTS

CROSS-REFERENCE TO RELATED APPLICATION

The present application is a 35 U.S.C. §371 national phase application from, and claiming priority to, International Application No. PCT/US2010/020505, filed Jan. 8, 2010, and published under PCT Article 21(2) in English, which is entitled to priority under 35 U.S.C. §119(e) to U.S. Provisional Application No. 61/143,394, filed Jan. 8, 2009, all of which applications are hereby incorporated by reference herein in their entireties.

STATEMENT REGARDING FEDERALLY SPONSORED RESEARCH OR DEVELOPMENT

This invention was made with government support under Grant No. R01 GM38148, awarded by the National Institutes of Health. The Government has certain rights in the invention.

BACKGROUND OF THE INVENTION

Most flowering plants produce perfect flowers containing both the male organs (stamens) and female organs (pistils). In maize, which has physically separated male and female inflorescences, floral meristems become unisexual through sex determination (Dellaporta & Calderon-Urrea, 1994, Science 266:1501; Irish, 1996, Bioessays 18:363). The basic unit of the maize inflorescence, called a spikelet, contains one upper and one lower flower (known as florets in grasses). Each floret initiates a series of floral organs including three stamen primordia and a central pistil primordium (Bonnet, 1940, J. Agric. Res. 60:25; Kiesselbach, "The Structure and Reproduction of Corn," Univ. of Nebraska Press, Lincoln, Nebr., 1949). These initially bisexual florets become exclusively staminate in the tassel (by abortion of pistil primordia) and exclusively pistillate in the ear (by arrest of developing stamens) (Bonnet, 1940, J. Agric. Res. 60:25; Cheng et al., 1983, Am. Bot. 70:450). Each ear spikelet produces a solitary functional pistil in the upper floret due to abortion of the pistil in the lower floret (Bonnet, 1940, J. Agric. Res. 60:25; Kiesselbach, "The Structure and Reproduction of Corn," Univ. of Nebraska Press, Lincoln, Nebr., 1949; Cheng et al., 1983, Am. Bot. 70:450).

Mutations altering the sexual fate of florets in maize indicate that sex determination is under genetic control. The non-homeotic tasselseed (ts) mutations ts1 and ts2 result in the conversion of the tassel inflorescence from staminate to pistillate (Emerson, 1920, J. Hered. 11:65; Nickerson & Dale, 1955, Ann. Mo. Bot. Gard. 42:195). Both ts1 and ts2 are required to eliminate pistil primordia through cell death (Calderon-Urrea & Dellaporta, 1999, Development 126:435; Kim et al., 2007, Genetics 177:2547). The ts2 gene encodes a short-chain dehydrogenase/reductase (DeLong et al., 1993, Cell 74:757) with broad activity, which has complicated the discovery of its natural substrate (Wu et al., 2007, FEBS J. 274:1172). It is unknown how is genes mediate pistil cell death, although it has been suggested that the dehydrogenase/reductase activity of ts2 may produce a pro-apoptotic signal or metabolize a substrate required for cell viability (Calderon-Urrea & Dellaporta, 1999, Development 126:435; Wu et al., 2007, FEBS J. 274:1172). Even less is known about the ts1 gene. TS2 transcripts are low or undetectable in ts1 mutant tassels, which suggests that ts1 may act upstream of ts2 by regulating ts2 RNA levels and possibly other sex determination genes (Calderon-Urrea & Dellaporta, 1999, Development 126:435).

Chemicals have been used to modulate and modify sexual differentiation in plants. The plant hormone ethylene has been observed to promote feminization in cucumber (Yamasaki et al., 2005, Vitam. Bonn. 72:79). Recent genetic and biochemical evidence has confirmed the role of ethylene in sex determination of melon, a related species (Boualem et al., 2008, Science 321:836). Conversely, gibberellin has masculinizing effects in cucumber but promotes feminization in maize (Bensen et al., 1995, Plant Cell 7:75), and auxin also has opposing effects in cucumber and *Mercurialis annua* (Yamasaki et al., 2005, Vitam. Horm. 72:79). However, little is known at this point about the role that chemicals play in sexual development and maturation of plants.

There is thus a great interest in identifying chemical compounds that modulate sexual differentiation in plants. Such compounds would be useful in suppressing or enhancing specific sexual phenotypes in plants, allowing the control of vast groups of plants without the need for time-consuming mechanical manipulation of the plants. The present invention fulfills these needs.

BRIEF SUMMARY OF THE INVENTION

The invention includes an agriculturally compatible composition comprising an effective amount of a compound selected from the group consisting of jasmonic acid, a jasmonic acid derivative, and a salt thereof. In one aspect, the derivative is a jasmonic acid ester. In another aspect, the derivative is jasmonic acid methyl ester or methyl jasmonate.

The invention also includes a method of modulating sexuality in a plant. The method comprises the step of administering to the plant an agriculturally compatible composition comprising an effective amount of a compound selected from the group consisting of jasmonic acid, a jasmonic acid derivative, and a salt thereof.

The invention also includes a method of suppressing complete feminization or restoring male sexuality in a plant with a ts1 or ts2 mutation. The method comprises the step of administering to the plant an agriculturally compatible composition comprising an effective amount of a compound selected from the group consisting of jasmonic acid, a jasmonic acid derivative, and a salt thereof.

The invention also includes a method of creating homozygous stock in a plant with a ts1 or ts2 mutation. The method includes the step of administering to the plant an agriculturally compatible composition comprising an effective amount of a compound selected from the group consisting of jasmonic acid, a jasmonic acid derivative, and a salt thereof, wherein the progeny of the plant is homozygous for the mutation and is male-sterile.

In one aspect, the derivative is jasmonic acid methyl ester.

In one aspect, the plant is grass-related. In another aspect, the plant is maize or rice. In yet another aspect, the plant is maize.

In one aspect, the method of the invention further comprises the step of administering to the plant at least one additional compound useful for controlling plant sexuality. In another aspect, the at least one additional compound is selected from the group consisting of ethylene, gibberellin and auxin.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIGS. 2A-2C, is a series of images illustrating the structure of the ts1 gene and the ts1 mutant alleles. In FIG. 2A, hollow boxes at left and right are 5' and 3' untranslated regions (UTRs), respectively; darkened boxes are exons and angled lines are introns. Mutations in eight ts1 mutant alleles are positioned above the corresponding exons. Insertions are represented by inverted triangles and a single deletion by a triangle. In FIG. 2B, TS1 protein features include a predicted chloroplast transit peptide (cTP, on the left), the PLAT/LH2 beta-barrel (in the middle), and the lipoxygenase domain (on the right) as well as five conserved residues (HS01, H583, H770, N774, 1918) necessary for iron binding and the phenylalanine (F636) residue predicting 13-LOX regiospecificity. In FIG. 2C, Bayesian and maximum parsimony consensus tree of predicted type 2 13-lipooxygenases in angiosperms is displayed. The arrowhead indicates the position of the maize ts1-encoded lipoxygenase. Posterior probabilities from Bayesian inference and bootstrap support from maximum parsimony analysis less than 100% are displayed below internal nodes to the left and right of a slash, respectively. This subclade is part of a more extensive phylogenetic analysis shown in FIG. 5.

FIG. 4, comprising FIGS. 4A-4C, is a representation of the alignment of the TS 1 (SEQ ID NO:20) and TS 1b (SEQ ID NO:21) proteins to potato lipooxygenase H3 (StLOX5, SEQ ID NO:22) and soybean L-1 (GmLOX1, SEQ ID NO:23). StLOX5 is the closest TS 1 relative that has been biochemically characterized, while GmLOX1 is one of the best studied plant lipoxygenases. Sequences were aligned with ClustalW2 and the gray similarity shading style in the background was applied with Jalview with the BLOSUM62 color scheme. The ts1 CDS was predicted to encode a protein of 918 amino acids with a theoretical mass of 103 kDa. Predicted domains are shown surrounded by colored boxes: the chloroplast transit peptide (cTP, row 1), the PLAT/LH2 domain (rows 1-3) and the lipoxygenase domain (rows 3-10). The predicted cTP has different lengths in TS 1, TS1b and StLOX5, while GmL0X1, a type1 lipoxygenase, does not possess a cTP. Asterisks indicate the five conserved residues necessary for iron binding. The black arrowhead marks the phenylalanine residue predicting 13-LOX regiospecificity.

FIG. 5, comprising FIGS. 5A-5B, is a representation of the phylogenetic analysis of TS1 and selected plant lipoxygenases by Bayesian and Maximum Parsimony inference. Nearly identical tree topologies were generated by Bayesian and Maximum Parsimony (MP), When values are lower than 100%, posterior probabilities from Bayesian inference and bootstrap support from MP analysis were displayed below internal nodes to the left and right of a slash sign, respectively. The fourth box from the top surrounds the type 2 13- LOX clade, which includes ts1-encoded LOX (arrow). The clade groups lipoxygenases from both monocotyledons and dicotyledons, Several lipoxygenases from this clade have been experimentally shown to display 13-LOX regiospecificity (second box from the top) and/or to localize to chloroplasts (fourth box from the top). The other Glades in the tree contain type 1 lipoxygenases from: monocotyledons (third box from the top) with 9-LOX, 13-LOX or mixed regiospecificity; dicotyledons with 13-LOX regiospecificity (second box from the top); and dicotyledons with 9-LOX regiospecificity (first box from the top).

FIG. 6, comprising FIGS. 6A-6I, is a series of images relating to expression of ts1, ts1b and is 2 in maize. FIG. 6A illustrates the expression profile of ts1, ts1b, and ts2 in different maize tissues by quantitative RT-PCR on three biological replicates for each tissue. Results were plotted as the ratio to the lowest detected level (ts1b in root)±SE. The y axis is in logarithmic scale. FIGS. 6B to 6E illustrate RNA in situ hybridization targeting the 3'UTR of ts1 (dark purple) in developing inflorescences. Scale bars, 200 mm. FIGS. 6B and 6C illustrate wild-type heterozygote male inflorescences (tassels) of 1.6 and 1.5 cm, respectively. FIG. 6D illustrates wild-type female inflorescence (ear) of 1.5 cm. FIG. 6E illustrates homozygous ts1-Mu01 deletion mutant tassel showing no hybridization signal. FIGS. 6F to 6I illustrate co-localization of TS1:mCherry and bcSnt:GFP fusion proteins in plastids of transfected onion epidermal cells. Scale bars, 50 mm. FIG. 6F illustrates TS1:mCherry red fluorescence (shown as gray color). FIG. 6G illustrates RbcSnt:GFP green fluorescence (shown as gray color). FIG. 6H illustrates the merge of Ts1:mCherry and RbcSnt:GFP plus two additional channels: 4',6'-diamidino-2-phenylindole (blue fluorescence, shown as large grey spots) for distinguishing nuclei, and differential interference contrast (DIC) for displaying cellular morphology. FIG. 6I illustrates the scatterplot of pixel gray value frequencies for RbcSnt:GFP (x axis) and Ts1:mCherry (y axis) channels. Frequencies were displayed using a rainbow lookup table (bottom, units between 0 and 255). Region 3 (upper right) contains pixels with signal above background in both channels, and a linear correlation in this region is a qualitative indicator of co-localization.

FIG. 7, comprising FIGS. 7A-7E, illustrate the determination of linoleic acid oxidation products in maize. FIG. 7A illustrates the partial gas chromatography-MS chromatograms displaying linoleic acid oxidation products generated by crude extracts of wild-type W22 tassels (light line) but not ts1-ref tassels (dark line). HPLC analysis of oxidation products (inset) indicated that the lipid hydroperoxide (HOD) peak was a mixture of 9-hydroxy-10,12-octadecadienoic acid (9-HOD) and β-hydroxy-9,11-octadecadienoic acid (13-HOD). FIG. 7B is a series of box plots summarizing the distribution of jasmonic acid in three tassel sets. Circles represent individual measurements. Diamonds show the 95% confidence interval of the mean (horizontal blue line). +/+corresponds to inbred line W22. FIG. 6C illustrates the blank-treated mutant ts1 tassel. FIG. 6D illustrates JA-treated ts1 tassel. FIG. 6E illustrates JA-treated ts2 tassel.

FIG. 9, comprising FIGS. 9A-9D, illustrates additional phenotypes of JA-treated ts1 and ts2 mutant tassels. FIG. 9A illustrates ts1 bisexual spikelets contained both anthers (dark arrows) and pistils (light arrows) while glumes display numerous trichomes and anthocyanins ring at the base. Anthers emerging from ts1 (FIG. 9B) and ts2 (FIG. 9C) rescued spikelets. FIG. 9D illustrates blank-treated ts1 spikelets with short, glabrous glumes without anthocyanin ring at base.

DETAILED DESCRIPTION OF THE INVENTION

Figure 1:
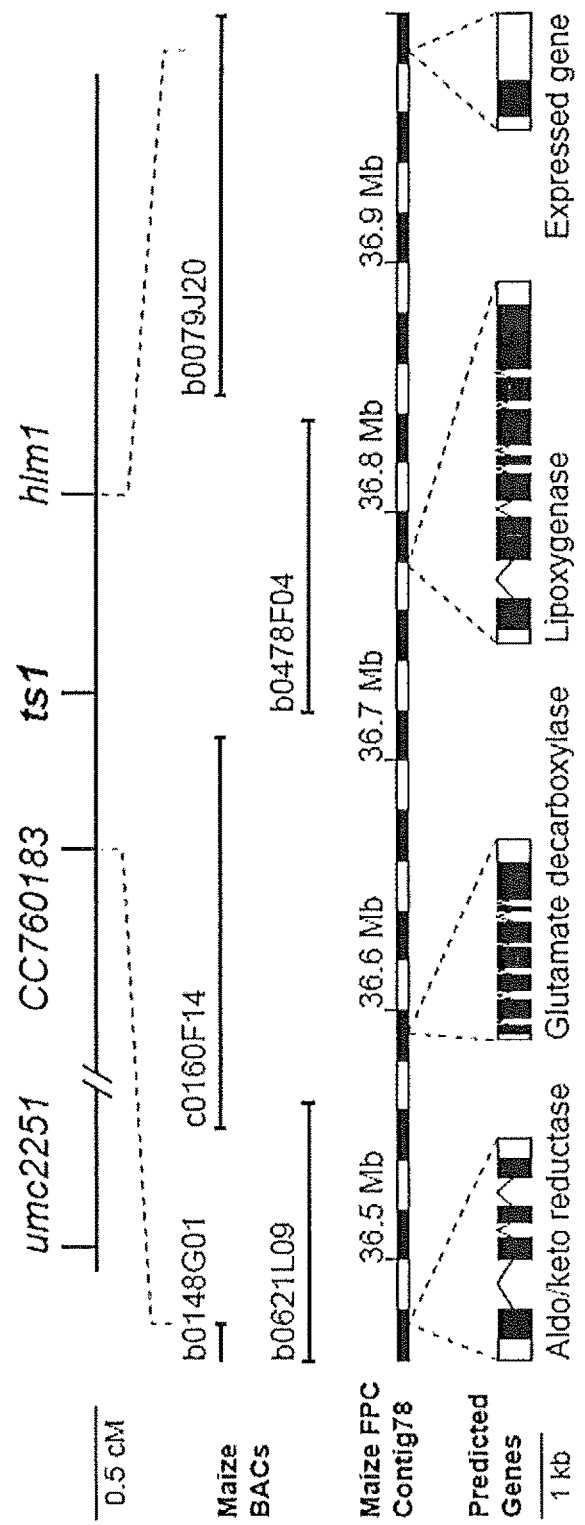
FIG. 1 is a series of images illustrating the genetic and physical map of the ts1 locus in maize chromosome 2.

The present invention relates to the discovery that certain compounds are useful for controlling the sexuality of plants.

In one aspect, these compounds act by restoring plant masculinization. In another aspect, these compounds suppress floral sexuality mutations and restore plant masculinization.

In one aspect, the invention provides an agriculturally compatible composition comprising a compound selected from the group consisting of jasmonic acid, a jasmonic acid derivative, and a salt thereof.

In another aspect, the invention provides a method of modulating sexuality in a plant. The method comprises the step of administering to the plant an agriculturally compatible composition comprising an effective amount of a compound selected from the group consisting of jasmonic acid, a jasmonic acid derivative, and a salt thereof.

In yet another aspect, the invention provides a method of suppressing complete feminization or restoring male sexuality in a plant with a ts1 or ts2 mutation. The method comprises the step of administering to the plant an agriculturally compatible composition comprising an effective amount of a compound selected from the group consisting of jasmonic acid, a jasmonic acid derivative, and a salt thereof.

In yet another aspect, the invention provides a method of creating homozygous stock in a plant with a ts1 or ts2 mutation. The method includes the step of administering to the plant an agriculturally compatible composition comprising an effective amount of a compound selected from the group consisting of jasmonic acid, a jasmonic acid derivative, and a salt thereof, wherein the progeny of the plant is homozygous for the mutation and is male-sterile.

In one embodiment, the derivative is a jasmonic acid ester. In another embodiment, the derivative is methyl jasmonate or jasmonic acid methyl ester.

In one embodiment, the plant is grass-related. In another embodiment, the plant is maize or rice. In yet another embodiment, the plant is maize.

In one embodiment, the method of the invention further comprises the step of administering to the plant at least one additional compound useful for controlling plant sexuality. In another aspect, the at least one additional compound is selected from the group consisting of ethylene, gibberelin and auxin.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used.

As used herein, the term "jasmonic acid derivative" refers to a derivative of jasmonic acid, such as but not limited to, a jasmonic acid ester. The class of jasmonic acid esters includes, but is not limited to, a jasmonic acid alkyl ester, jasmonic acid aryl ester, jasmonic acid heteroaryl ester, jasmonic acid aryalkyl ester, and jasmonic acid heteroaryl ester. The term "jasmonic acid derivative" also refers to chemical compounds that give rise to jasmonic acid or other jasmonic acid derivative by chemical or microorganism-based decomposition, regardless whether the decomposition takes place under controlled conditions or not.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the polypeptides include natural peptides, recombinant peptides, synthetic peptides or a combination thereof. A peptide that is not cyclic will have an N-terminus and a C-terminus. The N-terminus will have an amino group, which may be five (i.e., as a $NH_2$ group) or appropriately protected (for example, with a BOC or a Fmoc group). The C-terminus will have a carboxylic group, which may be free (i.e., as a COON group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, amino acids are represented by the full name thereof, by the three letter code corresponding thereto, or by the one-letter code corresponding thereto, as indicated below:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, which are generally not greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand;" sequences on the DNA strand which are located 5' to a reference point on the DNA are referred to as "upstream sequences;" sequences on the DNA strand which are 3' to a reference point on the DNA are referred to as "downstream sequences."

A "portion" of a polynucleotide means at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g. as a cDNA or a genomic or cDNA fragment produced by PCR or restriction enzyme digestion) independent of other sequences. It also includes a recombinant DNA which is part of a hybrid gene encoding additional polypeptide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "plant" refers to a living organism belonging to the kingdom Plantae. Examples of plants are grasses, such as switchgrass, rice, oats, wheat, barley, sorghum, millet, rye, triticale, buckwheat, fonio, quinoa, teff, wild rice, amaranth, kaniwa, spelt, einkorn, emmer, durum, and maize (corn). Preferably, the plant is rice or maize. Most preferably, the plant is maize.

As used herein, the term "effective amount" refers to a non-toxic but sufficient amount of an agent to provide the desired biological result. That result can be modulation of sexual differentiation in plants, suppression or enhancement of specific sexual phenotypes, or any other desired alteration of a plant phenotype. An appropriate effective amount in any individual case may be determined by one of ordinary skill in the art using routine experimentation.

As used herein, the term "agriculturally acceptable" refers to a material, such as a carrier or diluent, which does not abrogate the biological activity or properties of the compound, and is relatively non-toxic, i.e., the material may be administered to a plant without causing undesirable biological effects or interacting in a deleterious manner with any of the components of the composition in which it is contained.

As used herein, the term "agriculturally acceptable composition" refers to a mixture of at least one compound useful within the invention with agriculturally acceptable chemical components, such as carriers, stabilizers, diluents, dispersing agents, suspending agents, thickening agents, and/or excipients. The agriculturally acceptable composition facilitates administration of the compound to a plant. Multiple techniques of administering an agriculturally acceptable composition exist in the art including, but not limited to: watering, spraying, fumigation, aerolization, injecting, and dusting.

As used herein, the language "acceptable salt" refers to a salt of the administered compounds prepared from agriculturally acceptable non-toxic acids including inorganic acids, organic acids, solvates, hydrates, or clathrates thereof. The compounds useful within the invention may form salts with acids or bases, and such salts are included in the present invention. The term "salts" embraces addition salts of free acids or free bases of the compounds useful within the invention. Preferred salts are formed from cationic and anionic counterions that have been approved or validated for agricultural applications. Unacceptable salts may nonetheless possess properties such as high crystallinity, which have utility in the practice of the present invention, such as for example utility in process of synthesis, purification or formulation of compounds useful within this invention.

As used herein, the "instructional material" includes a publication, a recording, a diagram, or any other medium of expression that may be used to communicate the usefulness of the compounds described herein, In some instances, the instructional material may be part of a kit useful for effecting the alleviating or treating the various diseases or disorders recited herein. Optionally, or alternately, the instructional material may describe one or more methods of controlling plant sexuality. The instructional material of the kit may, for example, be affixed to a container that contains the compounds useful within the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

Compounds of the Invention

The compounds useful within the invention may be synthesized using techniques well-known in the art of organic synthesis or may be isolated from natural sources.

In one aspect, the compound is jasmonic acid ((1R,2R)-3-oxo-2-(2Z)-2-pentenylcyclopentaneacetic acid). In another aspect, the compound is a jasmonic acid ester. In yet another aspect, the compound is a jasmonic acid alkyl ester, jasmonic acid aryl ester, jasmonic acid heteroaryl ester, jasmonic acid aryalkyl ester, and jasmonic acid heteroaryl ester. Non-limiting examples of jasmonic acid esters are methyl jasmonate (or jasmonic acid methyl ester), ethyl jasmonate, n-propyl jasmonate, isopropyl jasmonate, n-butyl jasmonate, sec-butyl jasmonate, t-butyl jasmonate, methoxyethyl jasmonate, pentyl jasmonate, phenyl jasmonate, 4-chloro jasmonate, 4-fluoro jasmonate, naphtyl jasmonate, benzyl jasmonate, pyridinyl jasmonate, phenylethyl jasmonate and so on. In yet another aspect, the compound is methyl jasmonate (methyl (1R,2R)-3-oxo-2-(2Z)-2-pentenylcyclopentaneacetate).

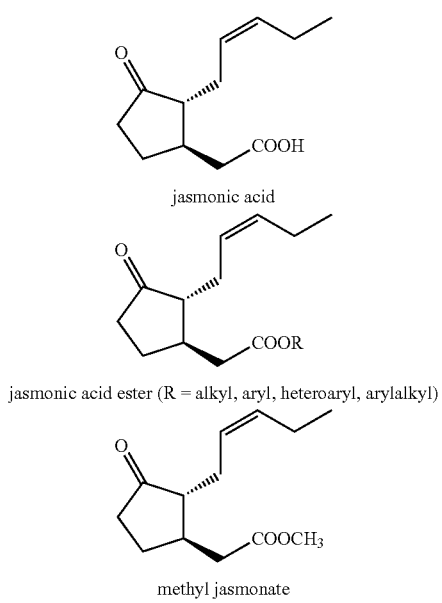

jasmonic acid jasmonic acid ester (R = alkyl, aryl, heteroaryl, arylalkyl)

methyl jasmonate

Acceptable base addition salts of compounds useful within the present invention include, for example, metallic salts and non-metallic salts. Metallic cationic counterions include alkali metal, alkaline earth metal and transition metal ions such as, for example, aluminum, bismuth, calcium, lithium, magnesium, neodymium, potassium, rubidium, sodium, strontium and zinc. Non-metallic cationic counterions include organic basic amines such as, for example, ammonium, benethamine [N-benzylphenethylamine], benzathine [N,N'-dibenzylethylenediamine], betaine [(carboxymethyl)trimethylammonium hydroxide], carnitine, clemizole [1-p-chloro-benzyl-2-pyrrolidin-1'-ylmethylbenzimidazole], chlorcyclizine [144-chloro-benzhydryl)-4-methylpiperazine], choline, dibenzylamine, diethanolamine, diethylamine, diethylammonium, diolamine, meglumine [N-ethylglucamine], erbumine [t-butylamine], ethylenediamine, heptaminol [6-amino-2-methylheptan-2-ol], hydrabamine [N,N'-di(dehydroabietyl)ethylenediamine], hydroxyethylpyrrolidine, imidazole, meglumine [N-methylglucamine], olamine, piperazine, 4-phenyl-cyclohexylamine, procaine, pyridoxine, triethanolamine, and tromethamine [tris(hydroxymethyl)aminomethane]. All of these salts may be prepared from the corresponding compound by reacting, for example, the appropriate acid or base with the compound.

Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic adds, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The compounds useful within the present invention may also be useful in combination with at least one additional compound useful for controlling plant sexuality, These additional compounds may comprise compounds described in the present invention or compounds, e.g., commercially available compounds, known to modify, modulate or alter plant sexuality.

In non-limiting examples, the compounds of the invention may be used in combination with at least one of the following compounds: ethylene, gibberellin and auxin.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul., 22: 27-55). Each equation referred to above may be applied to experimental data to generate a corresponding graph to aid in assessing the effects of the compound combination. The corresponding graphs associated with the equations referred to above are the concentration-effect curve, isobologram curve and combination index curve, respectively.

Administration/Dosage/Formulations

Routes of administration of any of the compositions of the invention include, but are not limited to, watering, spraying, fumigation, aerolization, injecting, or dusting. Administration may involve, in non-limiting examples, direct surface application to an intact or cut portion of the plant, microinjection into a tissue or cell thereof, or micro-bombardment, preferably under low pressure.

The regimen of administration may affect what constitutes an effective amount. The formulations of the invention may be administered to the plant at any stage of its development. Preferably, the formulations of the invention may be administered to the plant at the time of inflorescence development, during which the sex determination process is taking place. In the case of most lines of maize, this time corresponds to the period when the developing inflorescence reaches approximately 1.0 cm in height. At this stage of floral development, most maize plants possess 6-8 fully expanded leaves. This precise inflorescence height and expanded leaf number vary according to variety of maize and environmental growth conditions. Further, several divided dosages, as well as staggered dosages, may be administered daily or sequentially, or the dose may be continuously administered. Further, the dosages of the formulations may be proportionally increased or decreased as indicated by the exigencies of the situation.

Administration of the compositions of the present invention to a plant, preferably a grass-related plant, more preferably maize, may be carried out using known procedures, at dosages and for periods of time effective to modulate the plant sexuality. An effective amount of the compound necessary to achieve the desired sexuality modulation may vary according to factors such as the nature of the plant, its age, status and location; and the ability of the compound to modulate plant sexuality. Dosage regimens may be adjusted to provide the optimum response. For example, several divided doses may be administered daily or the dose may be proportionally reduced as indicated by the exigencies of the situation. A non-limiting example of an effective dose range for a compound useful within the invention is from about 0.001 to 1,000 mg/kg of plant weight/per day. In a non-limiting example, an individual plant is treated with 1 mL, of a 1 mM solution of a jasmonic acid derivative, and the treatment is performed three times at 48-hour intervals. One of ordinary skill in the art would be able to study the relevant factors and make the determination regarding the effective amount of the compound without undue experimentation.

Actual dosage levels of the active ingredients in the compositions of this invention may be varied so as to obtain an amount of the active ingredient that is effective to achieve the desired response for a particular plant, without being toxic to the plant.

A plant specialist, e.g., botanist or agricultural technician, having ordinary skill in the art may readily determine and prescribe the effective amount of the composition required. For example, the plant specialist could start doses of the compounds useful within the invention at levels lower than that required in order to achieve the desired effect and gradually increase the dosage until the desired effect is achieved.

In one embodiment, the compositions of the invention are formulated using one or more agriculturally acceptable excipients or carriers. In one embodiment, the compositions of the invention comprise an effective amount of a compound of the invention and an agriculturally acceptable carrier.

In one embodiment, the compositions of the invention are administered to the plant in dosages that range from one to five times at two-day intervals. In another embodiment, the compositions of the invention are administered to the plant in range of dosages that include, but are not limited to, once every day, every two, days, every three days to once a week, and once every two weeks. In another embodiment, the composition of the invention is applied once to the plant as a slow-release preparation. It will be readily apparent to one skilled in the art that the frequency of administration of the various combination compositions of the invention will vary from plant to plant, depending on many factors including, but not limited to, age, disease or disorder to be treated, gender, overall health, and other factors. Thus, the invention should not be construed to be limited to any particular dosage regime and the precise dosage and composition to be administered to any plant will be determined by the plant specialist based on the evaluation of the plant in question.

In one embodiment, the present invention is directed to a packaged agriculturally acceptable composition comprising a container holding an effective amount of a compound of the invention, alone or in combination with a second agricultural agent; and instructions for using the compound to modulate plant sexuality.

The term "container" includes any receptacle for holding the agriculturally acceptable composition. For example, in one embodiment, the container is the packaging that contains the agricultural composition. In other embodiments, the container is not the packaging that contains the agricultural composition, i.e., the container is a receptacle, such as a box or vial that contains the packaged agricultural composition or unpackaged agricultural composition and the instructions for use of the agricultural composition. Moreover, packaging techniques are well known in the art. It should be understood that the instructions for use of the agricultural composition may be contained on the packaging containing the agricultural composition, and as such the instructions form an increased functional relationship to the packaged product. However, it should be understood that the instructions may contain information pertaining to the compound's ability to perform its intended function, e.g., modulating plant sexuality.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Genetic Stocks and Mutants

Wild-type maize inbred lines W22, B73 and Mo17 were used. The ts1-ref allele was previously described (Emerson, 1920, J. Hered. 11:65; Emerson et al., 1935, Cornell Univ. Agric. Exp. Stn. Memoir 180). ts1-69-Alex-Mo17 was identified as a spontaneous mutant in Mo17; and ts1-0174 was discovered in an unknown genetic background. These three alleles were obtained from the Maize Genetics Cooperation Stock Center, Maize COOP (University of Illinois, Urbana/Champaign, Ill.). The ts1-MuSH and ts1-SH04 alleles were obtained from Plant Gene Expression Center, United States Department of Agriculture—Agricultural Research Service and the University of California, Albany, Calif.). The ts1-Mu92 and ts1-Mu93 alleles were recovered in progeny of self-pollinated maize plants known to contain active Mutator (Mu) elements (Monsanto, Creve Coeur, Mo.).

The remaining alleles, ts1-Mu01 and ts1-Mu02, were isolated by gene tagging over the course of several generations of testcrosses of ts1-ref/ts1-ref plants to Mutator lines. In brief, ts1-ref mutant plants were crossed to a W22 line carrying actively transposing Mu elements. Since ts1-ref is a recessive mutation, only wild-type plants are expected from such a cross unless a new ts1 mutant allele is recovered in any gametes of the Mu-active W22 line. About 40,000 individuals of this cross were grown during the summer seasons of 2001 and 2002. Plants showing a tasselseed phenotype, potentially containing new ts1 mutant alleles, were outcrossed to the W22 inbred line for at least two generations in order to segregate the new alleles and to reduce the number of active Mu elements in the genome. Additionally, these F1 plants were crossed to ts1-ref mutants to confirm allelism. The ts1-linked hlm1 marker was used to distinguish the new ts1 mutant alleles from the original ts1-ref allele in the first outcrossed generation. Homozygotes for the new allele were usually obtained in the third generation by self-pollinating heterozygous F2 plants.

ts1 Mapping Populations

Since the ts1 mutant plants are completely feminized, the ts1-ref stock was maintained by sib mating ts1-ref/ts1-ref with ts1-ref/Ts1. These sib makings were used to generate the original mapping population (n=93), which was selected for plants phenotypically scored as ts1/ts1 mutants. Any ts1-ref/ts1-ref plant carrying one or more of the linked molecular markers in a heterozygote state were deemed to be recombinant between the heterozygous marker and the ts1 locus. Once ts1 tightly-linked flanking markers were identified, they were subsequently used to screen three additional testcross populations containing both heterozygote wild-type plants and plants homozygous for the mutant ts1-ref allele. Two of these populations (n=119) also come from the sib mating ts1-ref/ts1-ref×ts1-ref/Ts1, while another mapping population (n=208) carried a wild-type Ts1 allele from the inbred W22 (ts1-ref/ts1-ref×ts1-ref/Ts1-W22).

Molecular Marker Development

Candidate marker sequences were selected through genetic, physical and rice-maize synteny mapping. These sequences usually corresponded to (a) maize BAC ends or ESTs deposited in GenBank (NIH; Benson et al., 2008, Nucleic Acids Research 36(Database issue):D25-30) ; or (b) rice genes annotated in the regions syntenic to maize intervals at Gramene (Cold Spring Harbor Laboratory, www dot gramene dot org). Candidate sequences were analyzed by BLAST through the TIGR Maize Database. Maize sequences corresponding to repetitive DNA were not further considered for marker design. Non-repetitive DNA sequences were selected for marker development and in some cases these sequences were extended by alignment with AZM sequences (TIGR).

Candidate marker sequences were PCR-amplified from genomic DNA of W22, ts1-ref/Ts1 and ts1-ref/ts1-ref plants. In a few instances, the PCR products had size polymorphisms easily resolved by agarose gel electrophoresis. In most cases, however, the PCR products had the same apparent size. In these cases, the PCR products were sequenced and examined for the presence of SNPs. If present, SNPs that represented differences in restriction enzyme recognition sites were used as CAPS (Cleaved Amplified Polymorphic Sequences) markers (Konieczny & Ausubel, 1993, Plant J. 4:403) to distinguish between the different alleles in the mapping population.

New markers were initially evaluated in 20 non-recombinant individuals of known phenotype to confirm co-segregation of the marker with the appropriate ts1 allele. This was necessary to prevent the use of markers corresponding to a duplicate region of the ts1 interval in chromosome 10 or to repeat sequences that have "escaped" filtering in the repeat database. Table 1 displays the features of the molecular markers defining the ts1 genetic region.

TABLE 1

Molecular markers used for mapping the ts1 locus

| Marker | Type * | Primer pair ID | Primer sequence (listed 5' to 3') | Product size (bp) † |
|---|---|---|---|---|
| CC760183 | CAPS (Tsp509I) | 1533 | CACAGGAGATTCTGTACTGTGACCA A (SEQ ID NO: 1) | 663 |
| | | 1541 | TGCAATGACAAGGGTATTCATGTG (SEQ ID NO: 2) | |
| hlm1 | CAPS (ScrFI) | 835 | CTCTCATAACACACACAAGCCTCT (SEQ ID NO: 3) | 1200 |
| | | 836 | AGCTACCTTTCTGGAGGGTGAAGAA (SEQ ID NO: 4) | |
| umc2251 ‡ | SSR | 1516 | CCTGAATCGCTCATTCGCTC (SEQ ID NO: 5) | 178 |
| | | 1517 | GTCGAGGGTTTGGAGGAGAGAC (SEQ ID NO: 6) | |

* CAPS, Cleaved Amplified Polymorphic Sequence; restriction enzymes used for CAPS marker analysis are indicated in parenthesis. SSR, Simple Sequence Repeat (Microsatellite)

† Size corresponds to the allele found in inbred line B73

‡ Previously reported SSR

Evaluation of PCR-Based Molecular Markers

PCR primers were designed with Primer3 (Rozen & Skaletsky, 2000, Methods Mol. Biol. 132:365) and synthesized by the W. M. Keck Foundation Biotechnology Resource Laboratory (Yale University, New Haven, Conn.). PCR-based markers were routinely amplified with Taq DNA polymerase (Qiagen, Valencia, Calif., USA) in 20 µL reactions containing 1×PCR buffer and 1× Q-Solution supplied by the manufacturer, 200 µM of each dNTP, 500 nM of each primer and 2.5 ng/µl genomic template DNA. Q-Solution contains the chemical betaine, which improves the amplification of DNA by reducing the formation of secondary structure in GC-rich regions. The addition of Q-Solution to the PCR reaction was mandatory for amplification of most maize sequences, which have high GC contents. Q-solution was excluded only for target sequences with <50% GC content. PCR cycling conditions were as follows: 95° C. (3 minutes); 35 cycles of 95° C. (30 seconds), 59-63° C. (30 seconds), 72° C. (1 minute/1 kb); 72° C. (10 minutes). Annealing temperature was variable, adjusted to 3 to 5° C. below the Primer3-calculated Tm of the primers used in each assay.

Southern Blot Analysis

Southern blot hybridization was performed with a published protocol (Dellaporta & Moreno, in "The Maize Handbook", M. Freeling, V. Walbot, Eds., Springer Verlag, New York, 1993, pp. 569-572), except that the hybridization solution consisted of 0.25 M sodium phosphate, pH 7.2 and 7% SDS, as suggested by the manufacturer of the Zeta-Probe GT blotting membranes (Biorad, Hercules, Calif., USA). The hybridization probe consisted of a 624 by fragment from the ts1-W22 gene (bases 2590-3213, spanning the end of exon 5 through the beginning of exon 7) and bore sufficient similarity to the duplicate ts1b gene (87-90%) so that both ts1 and ts1b were detected.

Phylogenetic Analysis

Sixty-four plant lipoxygenase amino acid sequences (Table 2), including that of TS1 and TS1b, were aligned with ClustalW2 (Chema et al., 2003, Nucleic Acids Res. 31:3497). Two different algorithms, maximum parsimony and Bayesian inference, were employed to estimate phylogenetic relationships of TS1 and related proteins. Maximum parsimony was implemented in PAUP*4.0b10 (Swofford, "PAUP*, Phylogenetic Analysis Using Parsimony (* and other methods)", Sinauer Associates, Sunderland, Mass., 1998) where the heuristic search option was applied with default values. Bootstrap values for the maximum parsimony tree were obtained by resampling 1,000 replicates under the full heuristic search method. Bayesian inference was performed with MrBayes 3.1.2 (Huelsenbeck & Ronquist, 2001, Bioinformatics 17:754) with a mixed amino acid substitution model, four independent chains run for 5,000,000 generations, and sampling every 1000th tree. Convergence was estimated when the standard deviation of split frequencies reached a plateau approaching zero, and the consensus tree was determined with a burn-in of 25% (1250 trees).

TABLE 2

Plant lipoxygenase sequences used in TS1 phylogenetic analysis

| Organism | Sequence ID | GenBank Accession |
| --- | --- | --- |
| Arabidopsis thaliana | AtLOX1 | Q06327 |
| | AtLOX2 | P38418 |
| | AtLOX3 | Q9SMW1 |
| | AtLOX4 | Q9FNX8 |
| | AtLOX5 | Q9FNX7 |
| | AtLOX6 | Q9CAG3 |
| Cucumis sativus | CsLOX2 | AAA79186 |
| | CsLOX3 | CAA63483 |
| | CsLOX4 | CAB83038 |
| Glycine max | GmLOX1 | P08170 |
| | GmLOX2 | P09439 |
| | GmLOX3 | P09186 |
| | GmLOX4 | P38417 |
| | GmLOX6 | AAA96817 |
| | GmLOX7 | P24095 |
| Hordeum vulgare | HvLOX1 | P93184 |
| | HvLOX2 | Q8GSM3 |
| | HvLOX3 | Q8GSM2 |
| | HvLOX4 | CAI84707 |
| | HvLOXA | P29114 |
| | HvLOXB | AAB60715 |
| | HvLOXC | AAB70865 |
| Lens culinaris | LcLOX1 | P38414 |
| Lycopersicon esculentum | LeLOX1 | P38415 |
| | LeLOX2 | P38416 |
| | LeLOX3 | AAG21691 |
| | LeLOX4 | Q96573 |
| | LeLOX5 | Q96574 |
| Nicotiana attenuata | NaLOX1 | AAP83136 |
| | NaLOX2 | AAP83137 |
| | NaLOX3 | AAP83138 |
| Nicotiana tabacum | NtLOX1 | CAA58859 |
| Oryza sativa | OsLOX1 | Q76I22 |
| | OsLOX10 | Q0DJB6 |
| | OsLOX2 | P29250 |
| | OsLOX2.3 | Q6H7Q6 |
| | OsLOX3 | Q7G794 |
| | OsLOX3b | Q53RB0 |
| | OsLOX5 | Q7XV13 |
| | OsLOX6 | Q8H0I6 |
| | OsLOX7 | P38419 |
| | OsLOX8 | Q84YK8 |
| | OsLOX9 | Q0IS17 |
| | OsLOXRCI1 | Q9FSE5 |
| Pisum sativum | PsLOX1 | AAB71759 |
| | PsLOX2 | P14856 |
| | PsLOX3 | P09918 |
| | PsLOX7 | CAC04380 |
| | PsLOX8 | CAA75609 |
| | PsLOX9 | CAG44504 |
| | PsLOXG | CAA53730 |
| Phaseolus vulgaris | PvLOX1 | P27480 |
| | PvLOX1b | AAB18970 |
| | PvLOX2b | AAG42354 |
| | PvLOX2c | AAF15296 |
| Solanum tuberosum | StLOX1 | CAA64765 |
| | StLOX2 | AAD09202 |
| | StLOX3 | AAB67865 |
| | StLOX4 | CAA65268 |
| | StLOX5 | CAA65269 |
| Zea mays | ZmLOX1 | AAL73499 |
| | ZmLOX2 | AAF76207 |

Quantitative RT-PCR analysis (qRT-PCR)

Maize plants from inbred line W22 were grown in the greenhouse. All tissue samples used for qRT-PCR assays were quickly dissected and immediately frozen in liquid nitrogen. Approximately 100 mg of frozen tissue were ground in a mortar and pestle and quickly re-suspended in 1 nil of Trizol® Reagent (Invitrogen, Carlsbad, Calif., USA). Developing inflorescences between 0.8 and 3 cm in length were directly placed in 1.5 ml microcentrifuge tubes, resuspended in 1 nil of Trizol® reagent and ground with a plastic pestle attached to a table top drill press. Total RNA was isolated according to manufacturer's recommendations and re-suspended in water previously treated with diethylpyrocarbonate (DEPC; Sigma, St. Louis, Mo., USA) containing 20 units of Protector RNase Inhibitor (Roche, Indianapolis, Ind., USA).

Prior to cDNA synthesis, 1 μg of total RNA was treated with 1 unit of DNase I, Amplification Grade (Invitrogen) in a 10 μl reaction containing 1× DNase I buffer supplied by the manufacturer. The reaction proceeded for 15 minutes at room temperature and the enzyme was inactivated by adding 1 μl of 25 mM EDTA and heating at 65° C. for 10 min, The DNase-treated RNA (1 μg) was directly used in cDNA synthesis with the SuperScript® 111 First-Strand Synthesis SuperMix for qRT-PCR (Invitrogen) following the manufacturer's instructions. The 2×RT Reaction Mix included both oligo(dT)20 and random hexamers to prime the reverse transcription reaction, The cDNA was diluted to 100 μl with 1×TE and stored at –80° C. PCR reactions were performed in optical 96-well plates with a 7500 Fast Real-Time PCR System sequence detection system (Applied Biosystems, Foster City, Calif., USA). Reactions contained 1× Power SYBR Green Master Mix reagent (Applied Biosystems), 300 nM of each gene-specific primer (Table 3) and 1 μl of diluted cDNA in a final volume of 25 μl. The standard thermal profile recommended by the manufacturer of the PCR master mix was followed. Three technical (PCR) replicates were set up for each one of the three biological replicates of each tissue sample. qRT-PCR data were normalized with actin1 as a reference gene.

TABLE 3

Primers used for quantitative qRT-PCR analysis

| Target gene | Primer pair TD | Primer sequence (listed 5' to 3') |
|---|---|---|
| actin1 | 213 | CATGAGGCCACGTACAACTCCATC (SEQ ID NO: 7) |
|  | 214 | TCATACTCTCCCTTGGAGATCCAC (SEQ ID NO: 8) |
| ts1 | 2221 * | GCTGCCGTACGAGCTCATGG (SEQ ID NO: 9) |
|  | 1894 | TCCTTTCAGATCATCTCTGTCATGC (SEQ 1D NO: 10) |
| ts1b | 2221 * | GCTGCCGTACGAGCTCATGG (SEQ ID NO: 11) |
|  | 2648 † | TTGGAGATCGGGGAGAAGACTAAA (SEQ ID NO: 12) |
| ts2 | 2264 | GTGGAGAAGATGGAGGAGGTGGT (SEQ ID NO: 13) |
|  | 2306 | ATTGATTCACAAGCCGATGAGGTT (SEQ ID NO: 14) |

* The specificity for ts1 and ts1b is achieved with the reverse primers P1894 and P2648, respectively
† P2648 is specific for the ts1-W22 allele In Situ Hybridization Primers P1930 (5'-CCTCTCAGTACCGACAGACAGC-3'; SEQ ID NO:15) and P1931 (5'-CCATTCAGTTCCTCA-CAGTCTTGC-3'; SEQ ID NO:16) were used to amplify a 217 by fragment of the ts1 gene corresponding to part of the 3' UTR. The PCR product was cloned into the pCRII-TOPO® vector (Invitrogen) generating pYU 1672, the plasmid used for synthesis of the ts1 in situ probe. The ts2 in situ hybridization probes have been previously described (DeLong et al., 1993, Cell 74:757) and are contained in the plasmids pYU59 and pYU60.

In situ hybridizations were performed as described (D. Jackson, in "Plant Molecular Pathology: A Practical Approach," S. J. Gurr, M. J. McPherson, D. J. Bowles, Eds., Oxford University Press, Oxford, 1992, vol. I, pp. 163-174) with modifications as described (Bortiri et al., 2006, Plant Cell 18:574). Three additional modifications were adopted: (a) no RNase treatment was performed after hybridizations; (b) the anti-DIG antibody was diluted 1/1000 and incubated for 2 hr at room temperature; (c) the buffer used for color detection included 10% polyvinyl alcohol (PVA) to increase reaction sensitivity.

Construction of a ts1:mCherry Fusion Gene

The mCherry gene was PCR amplified with PfuUltra™ High-Fidelity DNA Polymerase (Stratagene, La Jolla, Calif., USA) from the pREST-B mCherry vector (S12) with primers P2672 (5'-eggggtaccccATGGTGAGCAAGGGC-GAGGAGGAT-3; SEQ ID NO:17) and P2673 (5'-ctagtcta-gatggatccCTTGTACAGCTCGTCCATGCCGCC-3; SEQ ID NO:18), which added KpnI, NcoI and BamHI, XbaI sites respectively (lower case letters in primer sequences). The PCR product did not contain the endogenous stop codon, Instead, P2673 provided a new stop codon in the XbaI site downstream of the BamHI site. The PCR product was digested with KpnI and XbaI and the 733 by KpnI-XbaI mCherry fragment was gel purified. Plasmid pYU1721 was derived from the plant expression vector pRTL2 (Restrepo et al., 1990, Plant Cell 2:987) and contained the full-length ts1 CDS without the stop codon (ts1ΔSTOP) fused in frame with the gene encoding the monomer Red Fluorescent Protein (mRFP1) (construction details are available upon request). pYU1721 was digested with KpnI and XbaI to release the mRFP1 gene. The remaining ~6.5 kb plasmid containing pRTL2 plus the ts1ΔSTOP CDS was gel purified and ligated to the 733 by KpnI-XbaI mCherry gene. The resulting plasmid, pYU1743, was shown by sequencing to contain an in-frame N-terminus fusion of the ts1ΔSTOP CDS to the mCherry gene.

Biolistic Experiments in Onion Epidermal Cells

One microgram of plasmid DNA was precipitated on gold particles (1.0 μm, Biorad) essentially as described (Kleinet et al., 1987, Nature 327:70), Onion (*Allium cepa* L.) bulbs were cut in small pieces. The epidermal cell layers were carefully peeled and transferred to the surface of Petri dishes containing Murashige and Skoog basal medium (MS from Invitrogen, or Sigma-Aldrich, St. Louis, Mo. USA) solidified with 3.5% Phytagel (Sigma-Aldrich). Epidermal cell layers were bombarded with a Biolistic PDS1000/He Particle Delivery System (Biorad) with 1350 psi rupture discs. After bombardment the plates were incubated at 27° C. in darkness for 8-20 h. The epidermal cell layers were then stained for 10 minutes in 1 μg/ml DAPI dissolved in 1×PBS then washed for 10 minutes in 1×PBS and mounted in glass slides with 70% glycerol in 1×PBS.

Epifluorescence Microscopy, Photography and Image Analysis

Transformed cells were examined by epifluorescence microscopy with an Axioplan 2 microscope (Carl Zeiss Microimaging, Thornwood, N.Y., USA) with the appropriate excitation/emission filters. Differential Interference Contrast (DIC or Nomarski microscopy) was used to visualize cells under transmitted light. Digital images were captured with a Zeiss Axiocam with several Image Acquisition Modules of the Zeiss Axiovision software. The Multichannel Fluorescence module allowed the sequential acquisition of DAPI, GFP, mCherry and DIC images for each sample. The onion epidermal cell layer is very thick and not all cell features appear in the same focal plane. Therefore, a series of images over a defined z-focus range were acquired with the Z-Stack module of Axiovision. This module automatically calculated the distance between individual images of the z-stack to achieve the maximum axial resolution of the objective used. The Z-stack was reconstructed with the 3D Deconvolution module where the Regularized Inverted Filter (RIF) method was used. Final image display was completed by applying a maximum intensity projection (MIP) over the entire image volume within the context of the orthogonal slice view (Cut View). The Colocalization module was used to quantitatively assess the colocalization of the TS1:mCherry red fluorescent signal along with the RbcSnt:GFP green fluorescent signal.

Example 1

Positional Cloning and Mapping of ts1

The molecular marker hlm1 was isolated from the flanking sequence of a Mu4 element that was identified as tightly linked to the ts1-Mu92 mutation. The hlm1 marker was mapped approximately 1 cM from ts1 in a small testcross population (n=93) segregating for the ts1-ref allele. The maize ZMMBBb BAC library (CUGI) was probed with hlm1 and six BAC clones from contig 78 of the current maize physical map (Arizona Genomics Institute) were identified. A marker within this contig, umc2251, was tested for linkage and found to map distal to both ts1 and hlm1-8 and 9 cM respectively (FIG. 1). Therefore, the genetic interval containing ts1 was initially defined as a 9 cM region by the proximal hlm1 and the distal umc2251 markers. To further refine this interval, BAC end sequences in the physical region proximal to umc2251 were analyzed for potential low copy sequences. A molecular marker designed from the end sequence of BAC b0148G01 (CC760183) was tested and found to map 1 cM distal to ts1 (FIG. 1). A larger mapping population (total n=420) was analyzed with CC760183 and hlm1 and a total of 3 distal and 4 proximal recombinants to ts1 were detected. This analysis placed ts1 within a ~1.6 cM genetic interval defined by the proximal hlm1 and the distal CC760183 markers, which spanned a physical region of ~500 kb (FIG. 1).

A genomic sequence (AZM4_115428) corresponding to hind was identified in the TIGR AZM 4.0 assembly of the maize methyl-filtered and high-Cot genomic libraries which consists of sequences highly enriched for coding regions (Palmer et al., 2003, Science 302:2115; Whitelaw et al., 2003, Science 302:2118). Orthologs of CC760183 and AZM4_115428 were annotated in the rice genome delineating a 62 kb syntenic region that contained 9 predicted genes.

Example 2

Predicted Function of TS1 Protein

The ts1 gene was thus located in a region with extensive synteny with rice (Salse et al., 2004, Plant J. 38:396). Out of the nine genes contained in the ts1 syntenic interval within the sequenced genome of rice, no maize orthologs were found for four of these genes, and another three were mapped to locations unlinked to the ts1 locus in maize. Maize homologs of the remaining two rice genes, one encoding a putative glutamate decarboxylase and the other encoding a putative lipoxygenase, were confirmed to be contained within the ts1 physical interval (FIG. 1).

Figure 2C:
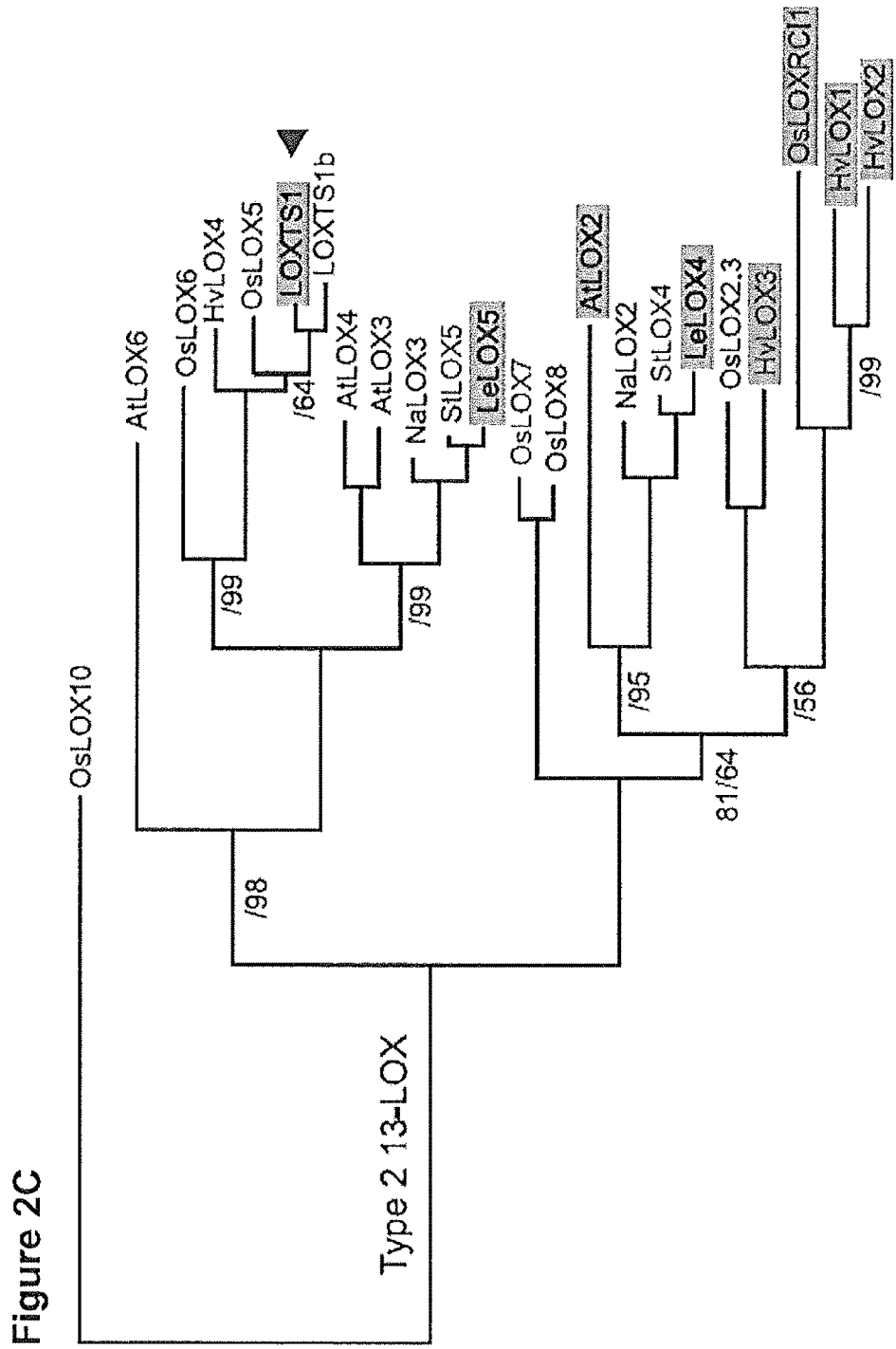
Figure 3:
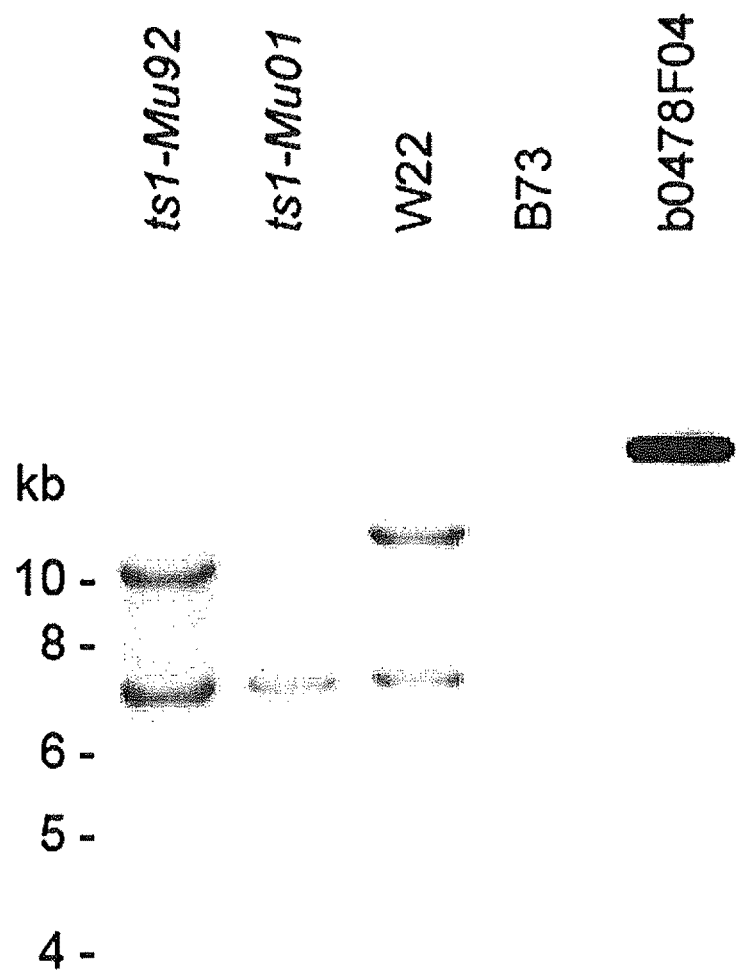
FIG. 3 is an image of the Southern blot hybridization of a ts1 probe to KpnI-digested genomic DNA from inbred lines W22 and B73 and ts1 mutant lines ts1-Mu92 and ts1-Mu01 along with plasmid DNA from BAC b0478F04. Both ts1 and ts1b are detected in the inbred lines and the mutant ts1-Mu92, while only ts1b is present in the a1 full-deletion mutant ts1-Mu01.

Sequencing showed that the gene encoding glutamate decarboxylase was monomorphic, whereas the gene encoding lipoxygenase in the ts1-ref line showed an 864-base pair (bp) insertion in the predicted first exon with complete linkage with the ts1 phenotype in mapping populations. To confirm that the lipoxygenase corresponded to the ts1 gene, eight ts1 mutant alleles were analyzed. Each contained an independent mutation in the gene encoding lipoxygenase (FIG. 2A, and Table 3). Complementary DNA sequence analysis showed that the ts1 gene contains seven exons with a coding sequence of 2757 by (FIG. 1A). A closely related gene was also identified in the database of the TIGR AZM 4.0 assembly and by Southern blot analysis (FIG. 3). This gene, named ts1b, has an identical exon-intron structure to that of ts1 and shares 93% nucleotide similarity. The ts1b gene is located on maize chromosome 10S, a segmental duplication of chromosome 2S (Gaut, 2001, Genome Res. 11:55). The TS1 protein displays 38 to 60% similarity to plant lipoxygenases and contains two conserved domains characteristic of this family: a beta-barrel (cd01751) and a catalytic helical bundle (pfam00305) (Shibata & Axelrod, 1995, J. Lipid Mediat. Cell Signal. 12:213) (FIG. 2B, and FIG. 4).

Figure 5B:
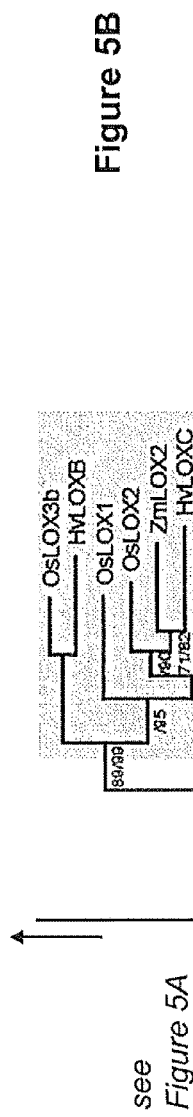

Lipoxygenases are non-heme iron-containing fatty acid dioxygenases that catalyze the peroxidation of polyunsaturated fatty acids such as linoleic acid, α-linolenic acid, and arachidonic acid. They are classified according to the positional specificity of linoleic acid oxygenation, which occurs at carbon 9 of the hydrocarbon backbone for the 9-LOX types and at carbon 13 for the 13-LOX types; a further subdivision (classes 1 and 2) has been recognized for 13-lipoxygenases without or with a putative chloroplast transit peptide (cTP), respectively (Feussner &Wasternack, 2002, Annu. Rev. Plant Biol. 53:275). According to ChloroP, a neural network-based method for predicting cTPs, the N-terminal 48 amino acids of the TS1 protein contain a cTP (Emanuelsson et al., 1999, Protein Sci. 8:978) (FIG. 2B, and FIG. 4). Additionally, TS1 contains a conserved phenylalanine (Phe636) previously identified as a determinant of 13-LOX regiospecificity (Hornung et al., Proc. Natl. Acad. Sci. U.S.A. 96:4192; Liavonchanka & Feussner, 2006, J. Plant Physiol. 163:348). Therefore, the primary structure of TS1 suggests that it is a member of the class 2 plastid-localized 13-lipoxygenases. This prediction was supported by Bayesian and maximum parsimony phylogenetic analyses of plant lipoxygenases, which placed TS1 and TS1b in a Glade including characterized and predicted class 2 13-lipoxygenase (FIG. 2C, and FIG. 5).

TABLE 3

Characterization of nine ts1 mutant alleles

| Allele | ts1 mutation (Sequences listed 5' to 3' on coding strand) | Genetic Location | background | Source |
|---|---|---|---|---|
| ts1-ref | 864 bp unknown insertion; 9 bp target site duplication (ACCCCCAGA) | 233-241 (exon 1) | Unknown | Emerson, 1920, J. Hered. 11: 65 |
| ts1-Mu93 | Mu8 insertion; 10 bp target site duplication (CGTTGACGGG) (SEQ ID NO: 19) | 932-941 (exon 2) | Unknown | P. Chomet & B. Lowe |

TABLE 3-continued

Characterization of nine ts1 mutant alleles

| Allele | ts1 mutation (Sequences listed 5' to 3' on coding strand) | Location | Genetic background | Source |
|---|---|---|---|---|
| ts1-0174 | 1828 bp unknown insertion; 6 bp target site duplication (GGCTTT) | 1020-1025 (exon 2) | Unknown | G. F. Sprague & COOP |
| ts1-Mu92 | C→G transversion; results in nonsense substitution Q288 > STOP | 1308 (exon 2) | Unknown | P. Chomet and B. Lowe |
| ts1-MUSH | MuDR insertion; 9 bp target site duplication (GGCTGCGGG) | 2032-2040 (exon 4) | Unknown | S. Hake |
| ts1-Alex | Single base pair deletion; results in frameshift | 2419 (exon 5) | Mo17 | D. E. Alexander/ Maize COOP |
| ts1-SH04 | Six by insertion (GAGAAG); results in extra glycine and glutamic acid | 3343-3344 (exon 7) | W22 | S. Hake |
| ts1Mu02 | ~3,600 by unknown insertion with 311 bp terminal repeats; 5 bp target site duplication (TCCAC) | 3655-3659 (exon 7) | W22 | this disclosure |
| ts1-Mu01 | Large deletion (unknown size) | — | W22 | this disclosure |

Example 3

Tissue-Specific Expression of ts1 and ts1b Genes

The tissue-specific expression of both ts1 and ts1b was established by quantitative reverse transcription polymerase chain reaction (RT-PCR) analysis of root, stem, leaf, tassel, and ear transcripts. The ts1 RNA was detected in all maize tissues examined, whereas ts1b RNA was detected at very low levels (less than that of ts1 by a factor of 90 to 500) (FIG. 6). The low expression of ts1b may explain why it does not also appear to be a component of sex determination in ts1 mutant plants. The broad expression of ts1 was unexpected because its mutant phenotype suggests a sex-specific function. Although no alterations in other tissues have been reported, it is possible that additional phenotypes for the ts1 mutation may be uncovered by more careful analyses. The ts2 gene was expressed almost as broadly as ts1, except in stem tissue, where expression was less than that of ts1 by a factor of ~35.

In situ hybridization showed that TS1 transcripts form stripes following the borders of the central inflorescence axis and projecting toward the spikelet attachment points (FIGS. 6B and 6D), In spikelet adaxial views, TS1 expression domains surround the spikelets, delineating their base (FIG. 6C). None of these expression patterns were observed in a homozygous ts1-Mu01 deletion mutant line containing a functional ts1 b gene (FIG. 6E). These observations indicate that TS1 transcripts subtend maize spikelets at their junction with the central inflorescence axis (rachis). This expression domain suggests a function for TS1, as metabolites synthesized through the lipoxygenase encoded by ts1 could act as diffusible signals affecting floral development in a non-cell-autonomous fashion.

The ChloroP-based prediction that TS1 localizes in plastids was confirmed with a fluorescent-tagged TS1 protein (TS1:mCherry) and a plastid-localized RbcSnt:GFP protein (Lee et al., 2002, Mol. Cells. 14:388). To quantitatively assess the colocalization of RbcSnt:GFP and TS1:mCherry fluorescent signals, correlation analysis of the intensity values of color (green and red) pixels in the dual-channel image was performed. Specifically, the Colocalization module in the Axiovision software (Carl Zeiss Microimaging, Thornwood, N.Y., USA) plotted the pixel grey values of fluorescent intensity of the x-axis and y-axis channels against each other (FIG. 6I). Then, correlation coefficients were calculated to measure the strength of the linear relationship between the two variables (Bolte & Cordelieres, 2006, J. Microsc. 224:213; Manders et al., 1992, J. Cell Sci, 103:857). The images in FIGS. 6E and 6F showed a Manders' overlap coefficient of 0.986 strongly indicating colocalization between the two signals. Additionally, weighted co-localization coefficients M1 and M2, which are independent of differences in fluorescence intensity between the two channels, were calculated. For TS1:mCherry, M2=0.906, indicating that a high proportion of red signal coincided with a signal in the green channel over its total intensity (Bolte & Cordelieres, 2006, J. Microsc. 224: 213; Manders et al., 1992, J. Cell Sci. 103:857). A similar conclusion was drawn for the weighted co-localization coefficient of RbcSnt:GFP (M1=0.903), indicating that TS1: mCherry protein is targeted to the same subcellular compartment as RbcSnt:GFP. TS1 is thus targeted to plant plastids.

Example 4

Analysis of Lipoxygenase Activity in Crude Protein Extracts from Tassel Inflorescences Frozen tassels were ground in liquid nitrogen and/or homogenized in a 1.5-ml microcentrifuge tube with 1 to 2 volumes of ice-cold 0.1 M Tris buffer, pH 7.5, containing 0.1 M NaCl, 5 mM EDTA, 0.1% β-mercaptoethanol, 0.6% Triton X-100, 1 mM PMSF and EDTA-free Protease Inhibitors (Roche, Indianapolis, Ind., USA), The mixture was clarified by centrifugation at 14,000×g for 30 minutes at 4° C. The supernatant was transferred to a new tube and total protein concentration estimated with the Micro BCA Protein Assay Kit (Pierce, Rockford, Ill., USA), Aliquots of crude protein extracts were added to 3 ml of potassium phosphate buffer, pH 6.0 containing 150 µM linoleic acid and stirred at 23° C. for 15 min. Peroxidation products were reduced to hydroxides, HOD) by adding 12 ml of a solution of 5 mg/ml $SnCl_2$ in ethanol and incubating for another 5 minutes at 23° C. Products isolated by extraction with diethyl ether were methyl-esterified and analyzed by GC-MS and HPLC. For all analyses, reference oxylipins of high chemical purity (Larodan Fine Chemicals, Malmö, Sweden) were used. Material to be analyzed by GC-MS was derivatized by treatment with trimethylchlorosilane/hexamethyldisilazane/pyridine (2:1:2, v/v/v) at room temperature for 15 min. Excess reagent and solvent were removed in vacuo and the residue was resuspended in hexane. GC-MS was carried out with a mass-selective detector (Hewlett-Packard model 5970B, Avondale, Pa., USA) connected to a gas chromatograph (Hewlett-Packard model 5890) equipped with a capillary column of 5% phenylmethylsiloxane (12 m, 0.33 µm film thickness). Helium was used as the carrier gas, and the column temperature was raised from 120° C. to 300° C. at 10° C./min.

SP-HPLC of methyl-esterified incubation products was carried out with a column of Nucleosil 50-5 (250×4,6 mm) purchased from Macherey-Nagel, Düren, Germany, and a solvent system of 0.6% 2-propanol/hexane at a flow rate of 2 ml/min. The absorbance (234 nm) and radioactivity of HPLC effluents were determined on-line with a Spectromonitor III ultraviolet detector (Laboratory Data Control, Riviera Beach, Fla., USA) and a liquid scintillation counter (IMUS Systems, Tampa, Fla., USA), respectively. Under the conditions used, the elution order of hydroxyoctadecadienoates were: methyl 13-hydroxy-9(Z), 11(E)-octadecadienoate (first), methyl 13-hydroxy-9(E),11(E)- octadecadienoate, methyl 9-hydroxy-10(E),12(Z)-octadecadienoate and methyl 9-hydroxy-10(E),12(E)-octadecadienoate (last).

Biochemical analysis of protein extracts from developing tassels for activity on the lipoxygenase substrate linoleic acid suggests that TS1 is capable of lipid peroxidation. Protein extracts from wild-type tassels catalyzed hydroperoxidation of linoleic acid, whereas no such activity was detected in mutant ts1-ref/ts-1ref developing tassels (FIG. 7). Mass spectrometry (MS) and high-performance liquid chromatography (HPLC) analyses showed that the products of this lipoxygenase activity are a mixture of 9- and 13-hydroperoxides in a 50:50 ratio (FIG. 7A); primary structure analysis had suggested that TS1 was a lipoxygenase with 13-regiospecifieity. Therefore, it is possible that TS1 possesses dual 9- and 13-regiospecificity—which has not previously been described for a plastid-localized lipoxygenase—or that TS1 function promotes the action of a separate 9-lipoxygenase.

Example 5

Quantification of Jasmonic Acid and Other Metabolites in Tassel Inflorescences

Figure 8:
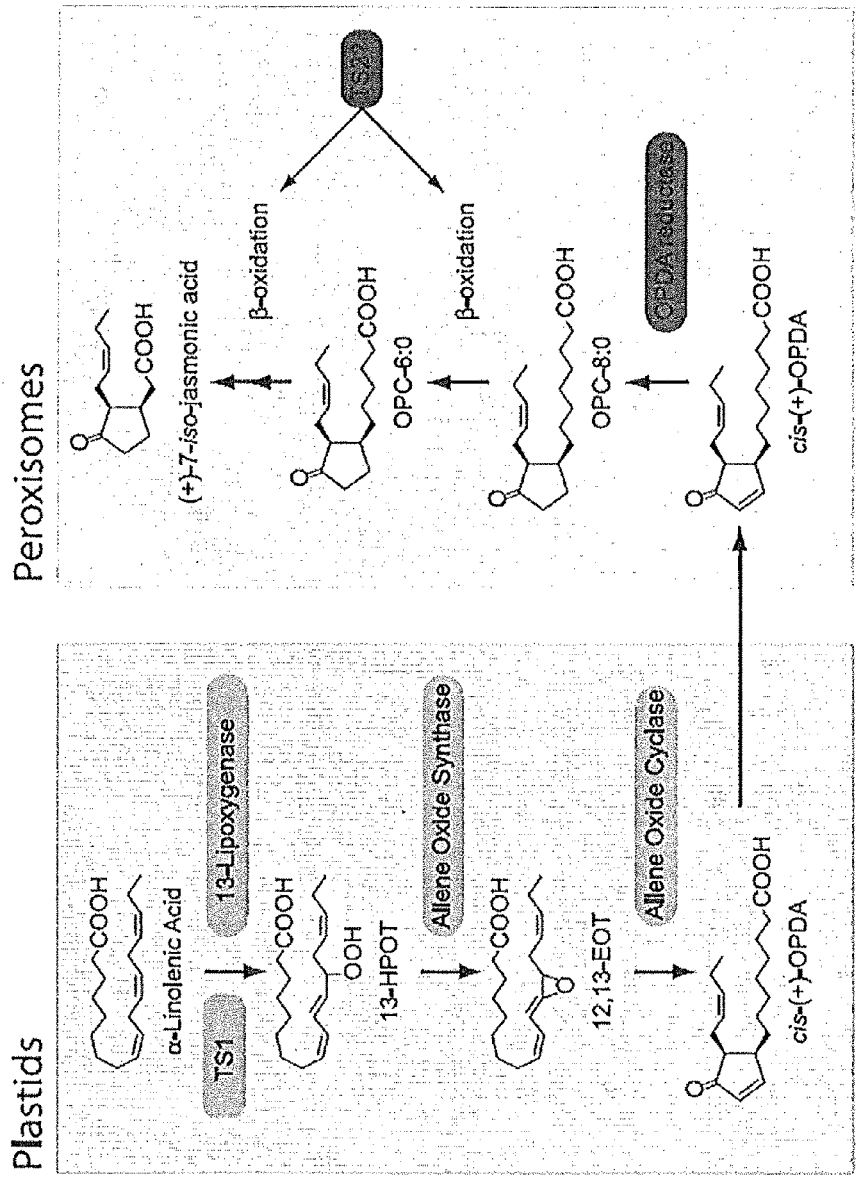
FIG. 8 illustrates the biosynthesis of jasmonic acid through the octadecanoid pathway.

Class 2 13-lipoxygenases participate in the biosynthesis of the plant hormone jasmonic acid (JA) (Wasternack, 2007, Ann. Bot. 100:681) (FIG. 8). The involvement of TS1 in JA biosynthesis was evaluated by measuring endogenous JA levels in developing wild-type and ts1-ref/ts1-ref mutant tassels.

As shown in FIG. 8, the first dedicated step in jasmonate biosynthesis is the peroxidation of α-linolenic acid (18:3) by 13-lipoxygenase to form (13S)-hydroperoxyoetadecatrienoic acid (13-HPOT). This is the putative function of TS1. 13-HPOT is transformed into the specific stereoisomer cis-(+)-12-oxophytodienoic acid (OPDA) through the sequential action of allene oxide synthase [yielding (13S)-12,13-epoxy-oetadecatrienoic acid (12,13-EOT)] and allene oxide cyclase. These steps in JA biosynthesis occur in plant plastids, where the corresponding enzymes are localized. Subsequent reactions occur in the peroxisomes. First, the cyclopentenone ring of OPDA is reduced to 12-oxophytoenoic acid (OPC-8) by OPDA reductase. Next, three β-oxidation cycles are proposed to shorten the carboxylic side chain of OPC-8 to produce the 12-carbon JA. A β-oxidation cycle is a set of four enzymatic reactions: oxidation, hydration, oxidation, and thiolysis. Not all enzymes acting on β-oxidation during JA biosynthesis have been identified. Because the oxidation in the third step is normally performed by a dehydrogenase activity, it is possible that TS2 may participate in this step of JA biosynthesis.

Maize plants of W22, ts1-ref/ts1-ref and ts1-ref/+ were field-grown during the summer of 2007. Developing tassel inflorescences between 0.8 and 3 cm in length were quickly dissected, placed in 1.5 ml microcentrifuge tubes and rapidly frozen in liquid nitrogen. Tissue samples were stored at −80° C. prior to solvent extraction. Jasmonic acid quantification was performed with vapor phase extraction for sample preparation and chemical ionization gas chromatography/mass spectrometry (CI-GC/MS) as described (Sehmelz et al., 2004, Plant J. 39:790). Descriptive and comparative statistics were obtained with Analyse-it® Standard edition (Analyse-it Software, Ltd, Leeds, England), an add-in for Microsoft Excel.

The average concentration of JA in wild-type and ts1-ref/+ heterozygotes was 44.2 T 13.9 ng per gram of fresh weight (ng/g FW) and 40.3 T 20.2 ng/g FW, respectively (FIG. 7B). Homozygous ts1-ref/ts1-ref tassels showed an average JA concentration of 4.3 T 2.1 ng/g FW (FIG. 7B), significantly below that of the wild type in a Kruskal-Wallis test and pair vise comparisons with a Bonferroni correction (P<0.0001). The ts1 mutation thus appears to reduce JA levels by a factor of ~10, indicating a role for the hormone in the pistil cell death process. JA levels of wild-type and mutant ts1 tassels are similar to those of wounded and nonwounded maize seedlings, respectively (Engelberth et al., 2007, Mol. Plant. Microbe Interact. 20:707), which supports the notion that JA is actively synthesized during normal tassel development.

Example 6

Chemical Treatment of Maize Plants

Maize plants were grown under greenhouse conditions. Two seeds were planted in 2-gallon reusable pots containing Super-Fine Germinating Mix (Fafard, Agawam, Mass., USA) or Redi-earth Professional Growing Mix (Sun Gro, Bellevue, Wash., USA). Fertilization was performed with controlled release Osmocote Plus 15-9-12 (Scotts, Marysville, Ohio, USA) following the manufacturer recommendations. Additional watering was performed with 4% ammonium iron citrate (Sigma-Aldrich) every 2 weeks to prevent chlorosis. Greenhouse average temperatures were 28° C. (day) and 21° C. (night). Supplemental lightning was provided to achieve a 16:8 hour photoperiod yearlong.

Tassels of about 1 cm were considered to be at an ideal stage to initiate chemical treatments. Since a thick leaf whorl covers the maize tassel at this time of development, only a destructive dissection of the plant permits to assess with certainty the stage of tassel development (Bonnet, 1940, J. Agricult. Res. 60:25; Bonnet, 1948, Ann. Mo. Bot. Gard. 35:269).

Additionally, the sex determination phase was reached within a wide time window, between 28 and 46 days post-planting, depending on the growing conditions. Leaf number, node number or internode distance were not always reliable criteria to predict the tassel developmental stage.

Seedlings from a family segregating 1:1 for wild-type (ts1-ref/Ts1) and ts1 mutant (ts1-ref/ts1-ref) plants were genotyped for the Ts1 and ts1-ref alleles with a PCR-based assay. Forty-six days after planting, one ts1 and one heterozygote plant showing 6-8 fully expanded leaves were dissected and their tassels were shown to be approximately 1.0 cm in height. This was used as a rough estimate indicating that similar plants, as judged by height and leaf number, were at the right stage to receive chemical treatments. Jasmonic acid (JA, Sigma-Aldrich) was dissolved at a concentration of 200 mM in absolute ethanol and stored at −20° C. Prior to plant treatment, the JA stock solution was diluted to a concentration of 1 mM in deionized water. Control plants were treated with a 0.005% ethanol solution ("blank" treatment or negative control). One ml of the corresponding solution was applied into the apical leaf cavity of each plant. Treatments were performed three times at 48-hour intervals.

Figures 7C, 7D, 7E:
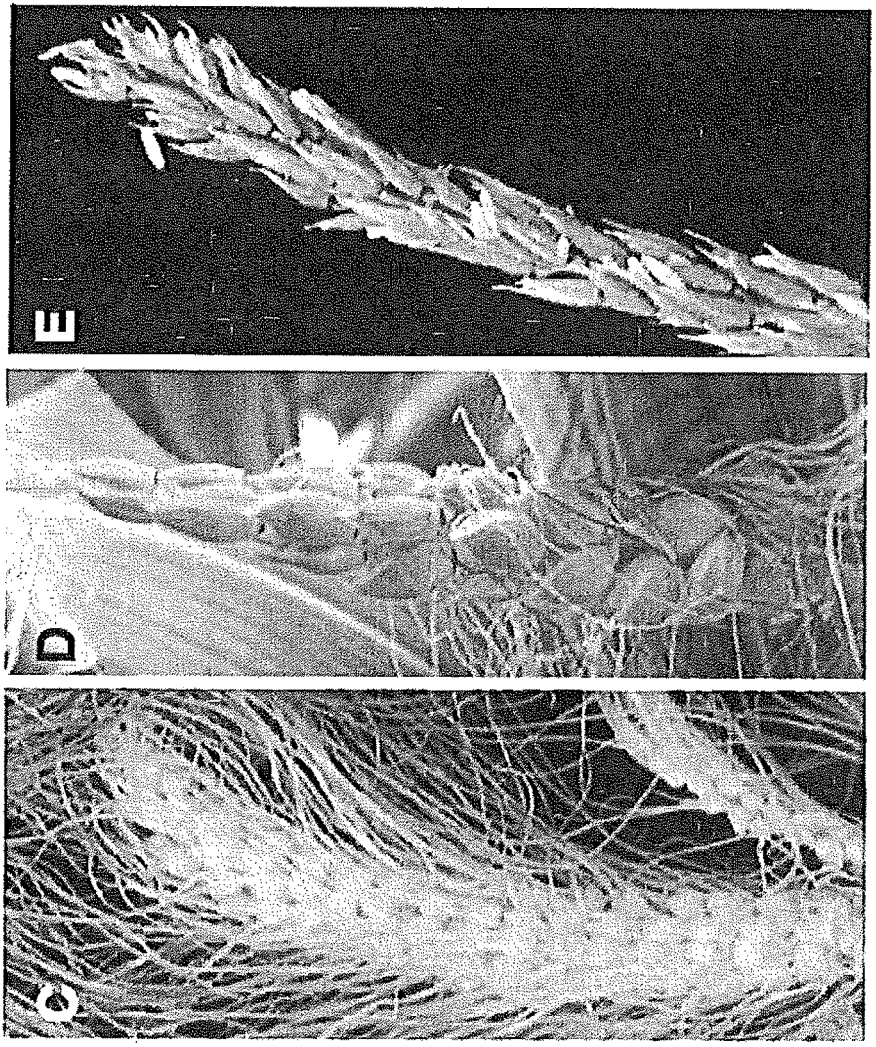

The developmental timing of the pistil abortion process occurs in tassel inflorescences when they are 1.0 to 3.0 cm in length (Irish & Nelson, 1993, Am. J. Bot. 80:292), which was also the stage at which ts1 expression occurred in the subtending glumes (FIGS. 6B to 6D). A 0.005% ethanol solution, with or without 1 mM JA, was applied to tassels of ~1 cm in wildtype (ts1-ref/+) or ts1 mutant (ts1-ref/ts1-ref) sibling plants. In ts1 mutant plants, JA application reversed feminization, as evidenced by the presence of staminate spikelets mostly in the mid- to apical regions (FIG. 7D). Wildtype rescue in ts1 mutants was observed in the appearance of subtending floral bracts (glumes) about 3 to 4 weeks after treatment. JA-treated glumes in ts1 mutants were elongated, were covered with numerous trichomes, and had a ring of anthocyanin deposited at the base (FIG. 7D), all three characteristics of wild-type staminate spikelets. Later in floral development, stamens emerged from JA-treated ts1 mutant spikelets (FIG. 9B).

Staminate florets from rescued IA-treated ts1/ts1 plants produced viable pollen, which was used for both self-pollination and test crosses to untreated ts1/ts1 mutant sibs. All test cross progeny (n>100) were homozygous for the ts1-ref allele and displayed a complete ts1 mutant phenotype. The JA-rescued phenotype of the tassel inflorescence was incomplete in that some spikelets were bisexual (FIG. 9A), containing both pistils and stamens, and others (mainly those located at the base of the inflorescence) were pistillate. These effects, however, may have been due to the timing of JA treatments, because the stage of floral maturation differs in a positionally dependent fashion throughout the inflorescence. Rescued staminate spikelets were never observed in blank-treated ts1-ref/ts1-ref plants (FIG. 7C; FIG. 9D, and Table 4), nor did JA treatment affect heterozygous ts1-ref/+ sibs (Table 4). The similar phenotype of ts1 and ts2 mutations indicates that both genes may act in the same metabolic pathway. Therefore, JA was also applied to mutant ts2-ref/ts2-ref and ts2-ref/+ plants, which responded in the same manner as the JA-treated ts1 mutants (FIG. 7E; FIG. 9C; and Table 4). These results indicate that JA can restore the wild-type phenotype in both ts1 and ts2 mutant plants. Moreover, TS2 may have an unexpected role in IA biosynthesis, perhaps as one of the yet-unidentified enzymes catalyzing a series of β-oxidations in this metabolic pathway (FIG. 4).

Genes regulating meristem determinacy early in maize inflorescence development are expressed at the boundary of the meristem and the inflorescence axis rather than within the meristem itself. These genes, such as ramosa1, ramosa3, and barren stalk1 (Gallovatti et al, 2004, Nature 432:630; Satoh-Nagasawa et al., 2006, Nature 441:227; Vollbrecht et al., 2005, Nature 441:227), probably act non-cell-autonomously by producing a diffusible signal at the base of the meristem (Vollbrecht et al., 2005, Nature 441:227). Analogously, ts1 expression at the boundary of developing spikelet initials and inflorescence axis produce the hormone JA, which may diffuse within the spikelet to regulate sexual development. This situation parallels JA-mediated anther dehiscence in Arabidopsis, where JA biosynthetic genes are highly expressed in the anther filament where it signals development both in the filament and within the anther (Ishiguro et al., 2001, Plant Cell 13:2191; Sanders et al., 2000, Plant Cell 12:1041). The expression of ts2 is known to be reduced in ts/mutants (Calderon-Urrea & Dellaporta, 1993, Development 126:435). The finding that ts2 may be involved in the same biosynthetic pathway as ts1 is not necessarily at odds with previous observation, as most genes encoding enzymes of the JA biosynthetic pathway are transcriptionally up-regulated by JA in a characteristic positive feedback loop (Wasternack, 2007, Ann. Bot. 100:681).

JA signals plant responses to biotic and abiotic stresses (Wasternack, 2007, Ann. Bot. 100:68) and regulates plant developmental processes such as root growth (Staswicknet al., 1992, PNAS U.S.A. 89:6837) and mechanotransduction (Weiler et al., 1993, Phytochemistry 32:591). In Arabidopsis, JA is required for male fertility because pollen maturation and anther dehiscence are blocked in mutations that impair JA biosynthesis (Ishiguro et al., 2001, Plant Cell 13:2191; Sanders et al., 2000, Plant Cell 12:1041). JA may promote anther dehiscence by signaling degeneration of the stomium, a group of specialized cells that run along the length of the anther and are necessary for dehiscence (Sanders et al., 1999, Sex, Plant Reprod. 11:297). The present results imply a role for JA in maize sex determination, wherein JA is necessary for signaling the tasselseed-mediated pistil abortion and the acquisition of the male characteristics of staminate spikelets. The diverse mechanisms of hormonal control in plant sex determination support the notion that the systems have evolved independently multiple times (Ainswortyh et al., 1998, Curr. Top. Dev. Biol. 38:167).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of suppressing complete feminization in a maize plant with a tasselseed 1 (ts1) or tasselseed 2 (ts2) mutation, the method comprising administering to said maize plant with a ts1 or ts2 mutation an agriculturally compatible composition comprising an effective amount of jasmonic acid or a salt thereof, wherein said maize plant has a tassel ranging from about 0.8 cm to about 3 cm in length at the time of administration, and wherein administration of said jasmonic acid or a salt thereof to said maize plant suppresses complete feminization of said plant.

2. The method of claim 1, wherein male sexuality is restored in said maize plant.

3. A method of generating stock of a maize plant that is homozygous for a ts1 or ts2 mutation, the method comprising the steps of:

administering to a first maize plant that is homozygous for a ts1 or ts2 mutation an agriculturally compatible composition comprising an effective amount of jasmonic acid or a salt thereof, wherein said first maize plant has a tassel ranging from about 0.8cm to about 3 cm in length at the time of administration, thereby generating a treated maize plant, wherein complete feminization of said maize plant is suppressed, and breeding said treated maize plant with an untreated second maize plant homozygous for same said mutation, thereby obtaining progeny maize plants that are homozygous for said mutation.

4. The method of claims 1, wherein said maize plant has a tassel of about 1 cm in length at the time of administration.

5. The method of claim 3, wherein said first maize plant has a tassel of about 1 cm in length at the time of administration.

* * * * *

SEQUENCE LISTING

<160> NUMBER OF SEQ ID NOS: 23

<210> SEQ ID NO 1
<211> LENGTH: 26
<212> TYPE: DNA
<213> ORGANISM: Zea mays

<400> SEQUENCE: 1
cacaggagat tctgtactgt gaccaa        26

<210> SEQ ID NO 2
<211> LENGTH: 24
<212> TYPE: DNA
<213> ORGANISM: Zea mays

<400> SEQUENCE: 2
tgcaatgaca agggtattca tgtg          24

<210> SEQ ID NO 3
<211> LENGTH: 24
<212> TYPE: DNA
<213> ORGANISM: Zea mays

<400> SEQUENCE: 3
ctctcataac acacacaagc ctct          24

<210> SEQ ID NO 4
<211> LENGTH: 25
<212> TYPE: DNA
<213> ORGANISM: Zea mays

<400> SEQUENCE: 4
agctaccttt ctggagggtg aagaa         25

<210> SEQ ID NO 5
<211> LENGTH: 20
<212> TYPE: DNA
<213> ORGANISM: Zea mays

<400> SEQUENCE: 5
cctgaatcgc tcattcgctc               20

<210> SEQ ID NO 6
<211> LENGTH: 22
<212> TYPE: DNA
<213> ORGANISM: Zea mays

<400> SEQUENCE: 6
gtcgagggtt tggaggagag ac            22

<210> SEQ ID NO 7
<211> LENGTH: 24
<212> TYPE: DNA
<213> ORGANISM: Zea mays

<400> SEQUENCE: 7
catgaggcca cgtacaactc catc          24

<210> SEQ ID NO 8
<211> LENGTH: 24
<212> TYPE: DNA
<213> ORGANISM: Zea mays

<400> SEQUENCE: 8

```
tcatactctc ccttggagat ccac                                          24

<210> SEQ ID NO 9
<211> LENGTH: 20
<212> TYPE: DNA
<213> ORGANISM: Zea mays

<400> SEQUENCE: 9
gctgccgtac gagctcatgg                                               20

<210> SEQ ID NO 10
<211> LENGTH: 25
<212> TYPE: DNA
<213> ORGANISM: Zea mays

<400> SEQUENCE: 10
tcctttcaga tcatctctgt catgc                                         25

<210> SEQ ID NO 11
<211> LENGTH: 20
<212> TYPE: DNA
<213> ORGANISM: Zea mays

<400> SEQUENCE: 11
gctgccgtac gagctcatgg                                               20

<210> SEQ ID NO 12
<211> LENGTH: 24
<212> TYPE: DNA
<213> ORGANISM: Zea mays

<400> SEQUENCE: 12
ttggagatcg gggagaagac taaa                                          24

<210> SEQ ID NO 13
<211> LENGTH: 23
<212> TYPE: DNA
<213> ORGANISM: Zea mays

<400> SEQUENCE: 13
gtggagaaga tggaggaggt ggt                                           23

<210> SEQ ID NO 14
<211> LENGTH: 24
<212> TYPE: DNA
<213> ORGANISM: Zea mays

<400> SEQUENCE: 14
attgattcac aagccgatga ggtt                                          24

<210> SEQ ID NO 15
<211> LENGTH: 22
<212> TYPE: DNA
<213> ORGANISM: Zea mays

<400> SEQUENCE: 15
cctctcagta ccgacagaca gc                                            22

<210> SEQ ID NO 16
<211> LENGTH: 24
<212> TYPE: DNA
<213> ORGANISM: Zea mays
```

```
<400> SEQUENCE: 16
ccattcagtt cctcacagtc ttgc                                              24

<210> SEQ ID NO 17
<211> LENGTH: 35
<212> TYPE: DNA
<213> ORGANISM: Zea mays

<400> SEQUENCE: 17
cggggtaccc catggtgagc aagggcgagg aggat                                  35

<210> SEQ ID NO 18
<211> LENGTH: 41
<212> TYPE: DNA
<213> ORGANISM: Zea mays

<400> SEQUENCE: 18
ctagtctaga tggatccctt gtacagctcg tccatgccgc c                           41

<210> SEQ ID NO 19
<211> LENGTH: 10
<212> TYPE: DNA
<213> ORGANISM: Zea mays

<400> SEQUENCE: 19
cgttgacggg                                                              10

<210> SEQ ID NO 20
<211> LENGTH: 918
<212> TYPE: PRT
<213> ORGANISM: Zea mays

<400> SEQUENCE: 20
```

Met Ala Ser Ala Met Lys Leu Leu Gly Arg Ser Ser Leu Ala Ser Pro
1               5                   10                  15

Ala Ala Ala Ala Pro Gly Arg Glu Arg Gly Gly Pro Cys Phe Ala
            20                  25                  30

Ala Val Gly Arg Glu Gly Ser Ala His Arg Arg Ser Ser Leu Arg
        35                  40                  45

Ser Thr Ala Pro Val Gly Ala Leu Ala Glu Arg Val Val Thr Pro
    50                  55                  60

Ala Pro Pro Glu Arg Ala Gly Ala Gly Pro Glu Pro His Pro Gln
65                  70                  75                  80

Ser Val Ala Ala Arg Ala Val Thr Val Arg Arg Arg Lys Glu
                85                  90                  95

Asp Ala Lys Arg Arg Val Ala Glu Gln Leu Asp Ala Tyr Ala Asp Arg
                100                 105                 110

Val Gly Arg Ser Val Leu Leu Glu Leu Ile Ser Thr Glu Thr Asp Pro
            115                 120                 125

Arg Lys Gly Gly Pro Lys Lys Ser Arg Arg Ser Ala Leu Val Gly Trp
        130                 135                 140

Phe Glu Lys Lys Asp Val Lys Thr Glu Arg Val Val Tyr Thr Ala Asp
145                 150                 155                 160

Phe Thr Val Asp Gly Ser Phe Gly Glu Pro Gly Ala Val Thr Val Leu
                165                 170                 175

Asn Arg His Gln Arg Glu Phe Phe Ile Glu Ser Ile Val Val Glu Gly
            180                 185                 190

Phe Pro Ser Gly Pro Ala His Phe Thr Cys Asn Ser Trp Val Gln Pro

-continued

```
            195                 200                 205
Thr Arg Val Asp Arg Asn Pro Arg Val Phe Phe Thr Asn Lys Pro Tyr
210                 215                 220

Leu Pro Ala Glu Thr Pro Gly Leu Gln Glu Leu Arg Arg Gln Gln
225                 230                 235                 240

Leu Ser Asp Leu Arg Gly Glu Gly Ala Asp Thr Gly Glu Arg Ile
            245                 250                 255

Thr Asp Arg Val Trp Glu Tyr Asp Val Tyr Asn Asp Leu Gly Asn Pro
                260                 265                 270

Asp Lys Gly Ala Glu Phe Ala Arg Pro Val Leu Gly Gly Glu Gln Gln
            275                 280                 285

Leu Pro Tyr Pro Arg Arg Met Arg Thr Gly Arg Pro Lys Thr Ile Thr
290                 295                 300

Asp Asp Arg Ala Glu Ser Arg Val Glu Tyr Pro Glu Pro Ile Tyr Val
305                 310                 315                 320

Ser Arg Asp Glu Glu Phe Glu Asp Gly Lys Asn Glu Met Leu Ser Glu
                325                 330                 335

Gly Ala Leu Lys Ala Leu Leu His Asn Phe Met Pro Leu Leu Val Ser
            340                 345                 350

Ser Val Ser Pro Asp Ile Arg Asp Phe Ala Gly Phe His Asp Val Asp
            355                 360                 365

Asn Leu Phe Lys Glu Gly Leu Arg Leu Lys Gln Ala Leu Gln Asp Gln
370                 375                 380

Leu Phe Gln Lys Ile Pro Phe Val Arg Lys Ile Gln Glu Asn Ser Glu
385                 390                 395                 400

Gly Leu Leu Arg Tyr Asp Thr Pro Asp Ile Ile Lys Lys Asp Lys Phe
                405                 410                 415

Ala Trp Leu Arg Asp Asp Glu Phe Ala Arg Gln Ala Leu Ala Gly Ile
            420                 425                 430

Asn Pro Val Asn Ile Glu Arg Leu Gln Ala Phe Pro Pro Met Ser Lys
            435                 440                 445

Leu Asp Pro Ala Val Tyr Gly Pro Pro Glu Ser Ala Ile Thr Glu Glu
450                 455                 460

His Ile Ile Gly Gln Leu Asp Gly Met Ser Val Gln Gln Ala Leu Gln
465                 470                 475                 480

Asp Asp Arg Leu Tyr Met Leu Asp Tyr His Asp Ile Phe Met Pro Phe
                485                 490                 495

Leu Asp Arg Ile Asn Ala Leu Asp Gly Arg Lys Ala Tyr Gly Thr Arg
            500                 505                 510

Thr Leu Phe Phe Leu Thr Ala Ala Gly Thr Leu Lys Pro Ile Ala Ile
            515                 520                 525

Glu Leu Cys Leu Pro Pro Met Thr Asp Gly Cys Ala Arg Ala Lys Arg
530                 535                 540

Val Phe Thr Pro Pro Ala Asp Ala Thr Ser Asn Trp Leu Trp Gln Leu
545                 550                 555                 560

Ala Lys Ala His Val Cys Ser Asn Asp Ala Gly Val His Gln Leu Ile
                565                 570                 575

Asn His Trp Leu Arg Thr His Ala Ala Met Glu Pro Phe Ile Ile Ala
            580                 585                 590

Ala His Arg His Leu Ser Thr Met His Pro Ile Phe Lys Leu Leu Lys
            595                 600                 605

Pro His Met Arg Tyr Thr Leu Lys Ile Asn Ala Leu Ala Arg Gln Ile
610                 615                 620
```

```
Leu Ile Asn Gly Asp Gly Val Ile Glu Ser Gly Phe Thr Pro Gly Arg
625                 630                 635                 640

Tyr Cys Met Glu Met Ser Ser Phe Ala Tyr Arg Glu Leu Trp Arg Leu
                645                 650                 655

Asp Gln Glu Gly Leu Pro Ala Asp Leu Ile Arg Arg Gly Met Ala Val
            660                 665                 670

Glu Asp Pro Thr Gln Pro His Gly Leu Arg Leu Leu Ile Glu Asp Tyr
        675                 680                 685

Pro Tyr Ala Thr Asp Gly Leu Leu Leu Trp Ser Ala Ile Arg Arg Trp
    690                 695                 700

Cys Asp Ala Tyr Val Ala Met Tyr Tyr Pro Ser Asp Glu Ser Val Gln
705                 710                 715                 720

Gly Asp Thr Glu Leu Gln Ser Trp Tyr Arg Glu Ala Val His Thr Gly
                725                 730                 735

His Ala Asp Lys Arg Asp Ala Pro Trp Trp Pro Arg Leu Ser Thr Pro
            740                 745                 750

Ala Asp Leu Ala Ser Leu Leu Thr Thr Leu Leu Trp Leu Thr Ser Ala
        755                 760                 765

Gln His Ala Ala Leu Asn Phe Gly Gln Tyr Pro Leu Gly Gly Tyr Ile
    770                 775                 780

Pro Asn Arg Pro Pro Leu Met Arg Arg Leu Val Pro Ala Glu Gly Asp
785                 790                 795                 800

Pro Glu Tyr Ala His Leu Val Ala Asp Pro His Arg Phe Phe Leu Ser
                805                 810                 815

Ala Leu Pro Ser Leu Thr Gln Thr Thr Phe Met Thr Val Ile Asp
            820                 825                 830

Thr Leu Ser Thr His Ser Ala Asp Glu Gln Tyr Leu Gly Glu Arg Pro
        835                 840                 845

Asp Glu Ala Trp Thr Ala Asp Pro Ala Ala Leu Ala Ala Ala Arg Glu
    850                 855                 860

Phe Ala Asp Glu Val Arg Arg Ala Glu Glu Ile Glu Arg Arg Asn
865                 870                 875                 880

Ala Asp Thr Gly Arg Arg Asn Arg Cys Gly Ala Gly Val Leu Pro Tyr
                885                 890                 895

Glu Leu Met Ala Pro Thr Ser Gly Pro Gly Ile Thr Cys Arg Gly Val
            900                 905                 910

Pro Asn Ser Val Thr Ile
        915

<210> SEQ ID NO 21
<211> LENGTH: 916
<212> TYPE: PRT
<213> ORGANISM: Zea mays

<400> SEQUENCE: 21

Met Ala Ser Ala Met Glu Leu Leu Gly Arg Ser Phe Ala Pro Gly His
1               5                   10                  15

Ala Ala Ala Ala Pro Arg Arg Gly Gly Gly Pro Cys Phe Ala Ala Val
            20                  25                  30

Gly Arg Glu Gly Ser Gly Ala His Arg Arg Ser Ser Ser Ser Ser
        35                  40                  45

Ser Leu Arg Ser Thr Ala Pro Val Asp Ala Leu Ala Glu Arg Val Val
    50                  55                  60

Ala Pro Pro Glu Arg Ala Glu Ala Val Pro Pro Glu Pro Ser Val Ala
```

```
                65                  70                  75                  80
            Ala Arg Ala Val Val Thr Val Arg Arg Ser Arg Lys Arg Asp Ala Lys
                            85                  90                  95

Cys Arg Val Ala Glu Arg Leu Asp Ala Cys Ala Asp Trp Val Gly Arg
                            100                 105                 110

Ser Val Leu Leu Glu Leu Ile Ser Thr Glu Thr Asp Pro Arg Lys Gly
                            115                 120                 125

Gly Pro Lys Lys Ser Arg Arg Ser Ala Leu Val Gly Trp Phe Gly Glu
                130                 135                 140

Lys Asp Val Lys Ala Glu Arg Val Val Tyr Thr Ala Asp Phe Asn Val
            145                 150                 155                 160

Asp Gly Ser Phe Gly Glu Pro Gly Ala Val Ala Val Leu Asn Arg His
                                165                 170                 175

Gln Arg Glu Phe Phe Val Glu Ser Ile Val Val Glu Gly Phe Pro Ser
                            180                 185                 190

Gly Pro Ala His Phe Thr Cys Tyr Ser Trp Val Gln Pro Thr Arg Val
                            195                 200                 205

His Arg Asp Pro Arg Val Phe Phe Thr Asn Lys Pro Tyr Leu Pro Ala
                            210                 215                 220

Gln Thr Pro Pro Gly Leu Arg Glu Leu Arg Arg Leu Glu Leu Ser Asp
            225                 230                 235                 240

Leu Arg Gly Glu Gly Ala Gly Thr Gly Gly Glu Arg Arg Thr Thr Asp
                            245                 250                 255

Arg Val Trp Glu Tyr Asp Val Tyr Asn Asp Leu Gly Asn Pro Asp Met
                            260                 265                 270

Gly Ala Glu Phe Ala Arg Pro Ile Leu Gly Gly Asp Gln Gln Leu Pro
                        275                 280                 285

Tyr Pro Arg Arg Met Arg Thr Gly Arg Pro Lys Thr Phe Thr Asp Asp
                        290                 295                 300

Arg Ala Glu Ser Arg Val Glu Tyr Pro Glu Pro Ile Tyr Val Ser Arg
            305                 310                 315                 320

Asp Glu Glu Phe Glu Glu Gly Lys Asn Glu Met Leu Ser Glu Gly Ala
                            325                 330                 335

Leu Lys Ala Leu Leu His Asn Phe Met Pro Leu Leu Val Ser Ser Val
                        340                 345                 350

Ser Pro Asp Phe Arg Asp Phe Ala Gly Phe His Asp Val Asp Asn Leu
                        355                 360                 365

Phe Lys Glu Gly Leu Arg Leu Lys Gln Ala Leu Gln Asp Gln Leu Phe
                    370                 375                 380

Gln Lys Ile Pro Phe Val Arg Lys Val Gln Glu Asn Ser Glu Gly Leu
            385                 390                 395                 400

Leu Arg Tyr Asp Thr Pro Asp Ile Ile Lys Arg Asp Lys Phe Ala Trp
                                405                 410                 415

Leu Arg Asp Asp Glu Phe Ala Arg Gln Ala Leu Ala Gly Ile Asn Pro
                        420                 425                 430

Val Asn Ile Glu Arg Leu Gln Ala Phe Pro Pro Met Ser Lys Leu Asp
                        435                 440                 445

Pro Ala Val Tyr Gly Pro Pro Glu Ser Ala Ile Thr Glu Glu His Ile
                450                 455                 460

Ile Gly Arg Leu Asp Gly Met Ser Val Gln Gln Ala Leu Glu Asp Asn
            465                 470                 475                 480

Arg Leu Tyr Met Leu Asp Tyr His Asp Ile Phe Leu Pro Phe Leu Asp
                            485                 490                 495
```

```
Arg Ile Asn Ala Gln Asp Gly Arg Lys Ala Tyr Gly Thr Arg Thr Leu
            500                 505                 510

Phe Phe Leu Thr Gly Ala Gly Thr Leu Lys Pro Ile Ala Ile Glu Leu
            515                 520                 525

Arg Leu Pro Pro Met Thr Asp Gly Cys Ala Arg Ala Lys Arg Val Leu
            530                 535                 540

Thr Pro Pro Ala Asp Ala Thr Ser Asn Trp Leu Trp Gln Leu Ala Lys
545                 550                 555                 560

Ala His Val Cys Ser Asn Asp Ala Gly Val His Gln Leu Ile Asn His
                565                 570                 575

Trp Leu Arg Thr His Ala Cys Met Glu Pro Phe Ile Ile Ala Ala His
            580                 585                 590

Arg Gln Met Ser Ala Met His Pro Ile Phe Lys Leu Leu Lys Pro His
            595                 600                 605

Met Arg Tyr Thr Leu Lys Ile Asn Ala Leu Ala Arg Gln Ile Leu Ile
    610                 615                 620

Asn Gly Asp Gly Val Ile Glu Ser Gly Phe Thr Pro Gly Arg Tyr Cys
625                 630                 635                 640

Met Glu Met Ser Ser Phe Ala Tyr Arg Glu Leu Trp Arg Leu Asp Gln
                645                 650                 655

Glu Gly Leu Pro Ala Asp Leu Ile Arg Arg Gly Met Ala Val Glu Asp
            660                 665                 670

Pro Thr Lys Pro His Gly Leu Arg Leu Leu Ile Glu Asp Tyr Pro Tyr
        675                 680                 685

Ala Thr Asp Gly Leu Leu Leu Trp Ser Ala Ile Thr Arg Trp Cys Gly
        690                 695                 700

Ala Tyr Val Ala Thr Tyr Tyr Pro Ser Asp Glu Ser Val Gln Ala Asp
705                 710                 715                 720

Thr Glu Leu Gln Ser Trp Tyr Thr Glu Ala Val Gln Thr Gly His Ala
                725                 730                 735

Asp Lys Arg Gly Ala Pro Trp Trp Pro Arg Leu Thr Thr Pro Gly Asp
            740                 745                 750

Leu Ala Ser Leu Leu Thr Thr Leu Leu Trp Leu Thr Ser Ala Gln His
            755                 760                 765

Ala Ala Leu Asn Phe Gly Gln Tyr Pro Leu Gly Gly Tyr Ile Pro Asn
            770                 775                 780

Arg Pro Pro Leu Met Arg Arg Leu Val Pro Ala Glu Gly Asp Pro Glu
785                 790                 795                 800

His Ala His Leu Val Ala Asp Pro His Arg Phe Phe Leu Ser Ala Leu
                805                 810                 815

Pro Gly Leu Thr Gln Ala Thr Thr Phe Met Thr Val Ile Asp Thr Leu
            820                 825                 830

Ser Thr His Ser Ala Asp Glu Gln Tyr Leu Gly Glu Arg Pro Asp Glu
            835                 840                 845

Ala Trp Thr Ala Asp Pro Ala Ala Leu Ala Ala Glu Arg Glu Phe Ala
            850                 855                 860

Asp Glu Val Arg Arg Ala Glu Glu Ile Gly Arg Arg Asn Thr Asp
865                 870                 875                 880

Ala Gly Arg Arg Asn Arg Cys Gly Ala Gly Val Leu Pro Tyr Glu Leu
                885                 890                 895

Met Ala Pro Thr Ser Gly Pro Gly Ile Thr Cys Arg Gly Val Pro Asn
            900                 905                 910
```

Ser Val Thr Ile
        915

<210> SEQ ID NO 22
<211> LENGTH: 914
<212> TYPE: PRT
<213> ORGANISM: Solanum tuberosum

<400> SEQUENCE: 22

Met Ala Leu Ala Lys Glu Ile Met Gly Ile Ser Leu Leu Glu Lys Ser
1               5                   10                  15

Ser Ser Phe Met Asn Ser Ser Met Ala Leu Phe Asn Pro Asn Asn
            20                  25                  30

Tyr His Lys Glu Asn His Leu Trp Phe Asn Gln Gln Phe Gln Gly Arg
            35                  40                  45

Arg Asn Leu Ser Arg Arg Lys Ala Phe Arg Gln Ser Thr Met Ala Ala
    50                  55                  60

Ile Ser Glu Asn Leu Ile Lys Val Val Pro Glu Lys Ala Val Arg Phe
65                  70                  75                  80

Lys Val Arg Ala Val Val Thr Val Arg Asn Lys Asn Lys Glu Asp Leu
                85                  90                  95

Lys Glu Thr Ile Val Lys His Leu Asp Ala Phe Thr Asp Lys Ile Gly
            100                 105                 110

Arg Asn Val Thr Leu Glu Leu Ile Ser Thr Asp Met Asp Pro Asn Thr
        115                 120                 125

Lys Gly Pro Lys Lys Ser Asn Gln Ala Val Leu Lys Asp Trp Ser Lys
    130                 135                 140

Lys Ser Asn Leu Lys Thr Glu Arg Val Asn Tyr Thr Ala Glu Phe Ile
145                 150                 155                 160

Val Asp Ser Asn Phe Gly Asn Pro Gly Ala Ile Thr Val Thr Asn Lys
                165                 170                 175

His Gln Gln Glu Phe Phe Leu Gly Ser Ile Thr Ile Glu Gly Phe Ala
            180                 185                 190

Cys Gly Pro Val His Phe Pro Cys Asn Ser Trp Val Gln Pro Lys Lys
        195                 200                 205

Asp His Pro Gly Lys Arg Ile Phe Phe Ser Asn Gln Pro Tyr Leu Pro
    210                 215                 220

Asp Glu Thr Pro Ala Gly Leu Lys Ser Leu Arg Glu Arg Glu Leu Arg
225                 230                 235                 240

Asp Leu Arg Gly Asp Gly Lys Gly Val Arg Lys Leu Ser Asp Arg Ile
                245                 250                 255

Tyr Asp Tyr Asp Ile Tyr Asn Asp Leu Gly Asn Pro Asp Lys Gly Ile
            260                 265                 270

Asp Phe Ala Arg Pro Lys Leu Gly Gly Asp Asp Asn Val Pro Tyr Pro
        275                 280                 285

Arg Arg Cys Arg Ser Gly Arg Val Pro Thr Thr Asp Ile Ser Ala
    290                 295                 300

Glu Ser Arg Val Glu Lys Pro Asn Pro Thr Tyr Val Pro Arg Asp Glu
305                 310                 315                 320

Gln Phe Glu Glu Ser Lys Met Asn Thr Phe Ser Thr Ser Arg Leu Lys
                325                 330                 335

Ala Val Leu His Asn Leu Ile Pro Ser Leu Met Ala Ser Ile Ser Ser
            340                 345                 350

Asn Asn His Asp Phe Lys Gly Phe Ser Asp Ile Asp Asn Leu Tyr Ser
        355                 360                 365

```
Lys Gly Leu Leu Leu Lys Leu Gly Leu Gln Asp Glu Val Leu Lys Lys
    370                 375                 380

Leu Pro Leu Pro Lys Val Val Ser Ser Ile Lys Glu Gly Asp Leu Leu
385                 390                 395                 400

Lys Tyr Asp Thr Pro Lys Ile Leu Ser Lys Asp Lys Phe Ala Trp Leu
                405                 410                 415

Arg Asp Asp Glu Phe Ala Arg Gln Ala Ile Ala Gly Val Asn Pro Val
            420                 425                 430

Ser Ile Glu Lys Leu Gln Phe Phe Pro Val Ser Lys Leu Asp Pro
        435                 440                 445

Glu Ile Tyr Gly Pro Gln Glu Ser Ala Leu Lys Glu His Ile Leu
    450                 455                 460

Gly His Leu Asn Gly Met Thr Val Gln Glu Ala Leu Asp Ala Asn Lys
465                 470                 475                 480

Leu Phe Ile Val Asp His His Asp Val Tyr Leu Pro Phe Leu Asp Arg
                485                 490                 495

Ile Asn Ala Leu Asp Gly Arg Lys Ala Tyr Ala Thr Arg Thr Ile Phe
            500                 505                 510

Phe Leu Ser Asp Val Gly Thr Leu Lys Pro Ile Ala Ile Glu Leu Ser
        515                 520                 525

Leu Pro Gln Thr Gly Pro Ser Ser Arg Ser Lys Arg Val Val Thr Pro
    530                 535                 540

Pro Val Cys Ala Thr Gly Asn Trp Thr Trp Gln Ile Ala Lys Ala His
545                 550                 555                 560

Val Cys Ala Asn Asp Ala Gly Val His Gln Leu Val Asn His Trp Leu
                565                 570                 575

Arg Thr His Ala Ser Leu Glu Pro Phe Ile Leu Ala Ala His Arg Gln
            580                 585                 590

Leu Ser Ala Met His Pro Ile Tyr Lys Leu Leu Asp Pro His Met Arg
        595                 600                 605

Tyr Thr Leu Glu Ile Asn Gly Leu Ala Arg Gln Ser Leu Ile Asn Ala
    610                 615                 620

Asp Gly Val Ile Glu Ala Cys Phe Thr Pro Gly Arg Tyr Cys Met Glu
625                 630                 635                 640

Ile Ser Ala Ala Ala Tyr Lys Asn Trp Arg Phe Asp Leu Glu Gly Leu
                645                 650                 655

Pro Ala Asp Leu Ile Arg Arg Gly Met Ala Val Pro Asp Ser Thr Gln
            660                 665                 670

Pro His Gly Leu Lys Leu Leu Ile Glu Asp Tyr Pro Tyr Ala Ala Asp
        675                 680                 685

Gly Leu Met Ile Trp Gly Ala Ile Glu Ser Trp Val Arg Asp Tyr Val
    690                 695                 700

Asn His Tyr Tyr Pro Ser Ser Ala Gln Val Cys Ser Asp Arg Glu Leu
705                 710                 715                 720

Gln Ala Trp Tyr Ala Glu Thr Ile Asn Val Gly His Val Asp Leu Arg
                725                 730                 735

Asn Glu Glu Trp Trp Pro Thr Leu Ala Thr Pro Glu Asp Leu Ile Ser
            740                 745                 750

Ile Leu Thr Thr Leu Ile Trp Leu Ala Ser Ala Gln His Ala Ala Leu
        755                 760                 765

Asn Phe Gly Gln Tyr Pro Tyr Gly Gly Tyr Val Pro Asn Arg Pro Pro
    770                 775                 780
```

```
Leu Met Arg Arg Leu Ile Pro Asp Glu Asn Asp Pro Glu Tyr Ala Val
785                 790                 795                 800

Phe Leu Ala Asp Pro Gln Lys Tyr Phe Phe Ser Ala Leu Pro Ser Leu
            805                 810                 815

Leu Gln Ala Thr Lys Phe Met Ala Val Val Asp Thr Leu Ser Thr His
        820                 825                 830

Ser Pro Asp Glu Glu Tyr Leu Gly Glu Arg His Gln Pro Ser Thr Trp
    835                 840                 845

Thr Gly Asp Ala Glu Ile Val Glu Ala Phe Tyr Lys Phe Ser Ala Glu
850                 855                 860

Ile Gly Arg Ile Glu Lys Glu Ile Asp Glu Arg Asn Ala Asn Thr Lys
865                 870                 875                 880

Leu Lys Asn Arg Cys Gly Ala Gly Val Leu Pro Tyr Glu Leu Leu Ala
            885                 890                 895

Pro Ser Ser Gly Pro Gly Val Thr Cys Arg Gly Val Pro Asn Ser Val
            900                 905                 910

Ser Ile

<210> SEQ ID NO 23
<211> LENGTH: 839
<212> TYPE: PRT
<213> ORGANISM: Glycine max

<400> SEQUENCE: 23

Met Phe Ser Ala Gly His Lys Ile Lys Gly Thr Val Val Leu Met Pro
1               5                   10                  15

Lys Asn Glu Leu Glu Val Asn Pro Asp Gly Ser Ala Val Asp Asn Leu
            20                  25                  30

Asn Ala Phe Leu Gly Arg Ser Val Ser Leu Gln Leu Ile Ser Ala Thr
        35                  40                  45

Lys Ala Asp Ala His Gly Lys Gly Lys Val Gly Lys Asp Thr Phe Leu
    50                  55                  60

Glu Gly Ile Asn Thr Ser Leu Pro Thr Leu Gly Ala Gly Glu Ser Ala
65                  70                  75                  80

Phe Asn Ile His Phe Glu Trp Asp Gly Ser Met Gly Ile Pro Gly Ala
                85                  90                  95

Phe Tyr Ile Lys Asn Tyr Met Gln Val Glu Phe Phe Leu Lys Ser Leu
            100                 105                 110

Thr Leu Glu Ala Ile Ser Asn Gln Gly Thr Ile Arg Phe Val Cys Asn
        115                 120                 125

Ser Trp Val Tyr Asn Thr Lys Leu Tyr Lys Ser Val Arg Ile Phe Phe
    130                 135                 140

Ala Asn His Thr Tyr Val Pro Ser Glu Thr Pro Ala Pro Leu Val Ser
145                 150                 155                 160

Tyr Arg Glu Glu Glu Leu Lys Ser Leu Arg Gly Asn Gly Thr Gly Glu
                165                 170                 175

Arg Lys Glu Tyr Asp Arg Ile Tyr Asp Tyr Asp Val Tyr Asn Asp Leu
            180                 185                 190

Gly Asn Pro Asp Lys Ser Glu Lys Leu Ala Arg Pro Val Leu Gly Gly
        195                 200                 205

Ser Ser Thr Phe Pro Tyr Pro Arg Arg Gly Arg Thr Gly Arg Gly Pro
    210                 215                 220

Thr Val Thr Asp Pro Asn Thr Glu Lys Gln Gly Glu Val Phe Tyr Val
225                 230                 235                 240
```

```
Pro Arg Asp Glu Asn Leu Gly His Leu Lys Ser Lys Asp Ala Leu Glu
            245                 250                 255

Ile Gly Thr Lys Ser Leu Ser Gln Ile Val Gln Pro Ala Phe Glu Ser
        260                 265                 270

Ala Phe Asp Leu Lys Ser Thr Pro Ile Glu Phe His Ser Phe Gln Asp
    275                 280                 285

Val His Asp Leu Tyr Glu Gly Ile Lys Leu Pro Arg Asp Val Ile
290                 295                 300

Ser Thr Ile Ile Pro Leu Pro Val Ile Lys Glu Leu Tyr Arg Thr Asp
305                 310                 315                 320

Gly Gln His Ile Leu Lys Phe Pro Gln Pro His Val Val Gln Val Ser
                325                 330                 335

Gln Ser Ala Trp Met Thr Asp Glu Glu Phe Ala Arg Glu Met Ile Ala
            340                 345                 350

Gly Val Asn Pro Cys Val Ile Arg Gly Leu Glu Glu Phe Pro Pro Lys
        355                 360                 365

Ser Asn Leu Asp Pro Ala Ile Tyr Gly Asp Gln Ser Ser Lys Ile Thr
    370                 375                 380

Ala Asp Ser Leu Asp Leu Asp Gly Tyr Thr Met Asp Glu Ala Leu Gly
385                 390                 395                 400

Ser Arg Arg Leu Phe Met Leu Asp Tyr His Asp Ile Phe Met Pro Tyr
                405                 410                 415

Val Arg Gln Ile Asn Gln Leu Asn Ser Ala Lys Thr Tyr Ala Thr Arg
            420                 425                 430

Thr Ile Leu Phe Leu Arg Glu Asp Gly Thr Leu Lys Pro Val Ala Ile
        435                 440                 445

Glu Leu Ser Leu Pro His Ser Ala Gly Asp Leu Ser Ala Ala Val Ser
    450                 455                 460

Gln Val Val Leu Pro Ala Lys Glu Gly Val Glu Ser Thr Ile Trp Leu
465                 470                 475                 480

Leu Ala Lys Ala Tyr Val Ile Val Asn Asp Ser Cys Tyr His Gln Leu
                485                 490                 495

Met Ser His Trp Leu Asn Thr His Ala Ala Met Glu Pro Phe Val Ile
            500                 505                 510

Ala Thr His Arg His Leu Ser Val Leu His Pro Ile Tyr Lys Leu Leu
        515                 520                 525

Thr Pro His Tyr Arg Asn Asn Met Asn Ile Asn Ala Leu Ala Arg Gln
    530                 535                 540

Ser Leu Ile Asn Ala Asn Gly Ile Ile Glu Thr Thr Phe Leu Pro Ser
545                 550                 555                 560

Lys Tyr Ser Val Glu Met Ser Ser Ala Val Tyr Lys Asn Trp Val Phe
                565                 570                 575

Thr Asp Gln Ala Leu Pro Ala Asp Leu Ile Lys Arg Gly Val Ala Ile
            580                 585                 590

Lys Asp Pro Ser Thr Pro His Gly Val Arg Leu Leu Ile Glu Asp Tyr
        595                 600                 605

Pro Tyr Ala Ala Asp Gly Leu Glu Ile Trp Ala Ala Ile Lys Thr Trp
    610                 615                 620

Val Gln Glu Tyr Val Pro Leu Tyr Tyr Ala Arg Asp Asp Val Lys
625                 630                 635                 640

Asn Asp Ser Glu Leu Gln His Trp Trp Lys Glu Ala Val Glu Lys Gly
                645                 650                 655

His Gly Asp Leu Lys Asp Lys Pro Trp Trp Pro Lys Leu Gln Thr Leu
```

```
                        660                 665                 670
Glu Asp Leu Val Glu Val Cys Leu Ile Ile Ile Trp Ile Ala Ser Ala
        675                 680                 685

Leu His Ala Ala Val Asn Phe Gly Gln Tyr Pro Tyr Gly Gly Leu Ile
        690                 695                 700

Met Asn Arg Pro Thr Ala Ser Arg Arg Leu Leu Pro Glu Lys Gly Thr
705                 710                 715                 720

Pro Glu Tyr Glu Glu Met Ile Asn Asn His Glu Lys Ala Tyr Leu Arg
                725                 730                 735

Thr Ile Thr Ser Lys Leu Pro Thr Leu Ile Ser Leu Ser Val Ile Glu
            740                 745                 750

Ile Leu Ser Thr His Ala Ser Asp Glu Val Tyr Leu Gly Gln Arg Asp
        755                 760                 765

Asn Pro His Trp Thr Ser Asp Ser Lys Ala Leu Gln Ala Phe Gln Lys
        770                 775                 780

Phe Gly Asn Lys Leu Lys Glu Ile Glu Glu Lys Leu Val Arg Arg Asn
785                 790                 795                 800

Asn Asp Pro Ser Leu Gln Gly Asn Arg Leu Gly Pro Val Gln Leu Pro
            805                 810                 815

Tyr Thr Leu Leu Tyr Pro Ser Ser Glu Glu Gly Leu Thr Phe Arg Gly
            820                 825                 830

Ile Pro Asn Ser Ile Ser Ile
            835
```